(12) United States Patent
Doguet et al.

(10) Patent No.: US 11,318,301 B2
(45) Date of Patent: May 3, 2022

(54) CUFF ELECTRODE OR OPTRODE COMPRISING SOFT EDGES AND PROCESS FOR THE PRODUCTION THEREOF

(71) Applicant: Synergia Medical, Mont-Saint-Guibert (BE)

(72) Inventors: Pascal Doguet, Mont-Saint-Guibert (BE); Marie Dautrebande, Mont-Saint-Guibert (BE); Benoit Olbrechts, Mont-Saint-Guibert (BE); Gregory Thiebaut, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 0 days.

(21) Appl. No.: 16/769,337

(22) PCT Filed: Nov. 27, 2018

(86) PCT No.: PCT/EP2018/082703
§ 371 (c)(1),
(2) Date: Jun. 3, 2020

(87) PCT Pub. No.: WO2019/110378
PCT Pub. Date: Jun. 13, 2019

(65) Prior Publication Data
US 2020/0306526 A1 Oct. 1, 2020

(30) Foreign Application Priority Data
Dec. 4, 2017 (WO) .................. PCT/EP2017/081408

(51) Int. Cl.
*A61B 18/18* (2006.01)
*A61N 1/05* (2006.01)
(Continued)

(52) U.S. Cl.
CPC ......... *A61N 1/0556* (2013.01); *A61N 5/0601* (2013.01); *A61N 5/0622* (2013.01);
(Continued)

(58) Field of Classification Search
CPC .. A61N 1/0556; A61N 5/0601; A61N 5/0622; A61N 2005/063;
(Continued)

(56) References Cited

U.S. PATENT DOCUMENTS

| 4,602,624 A | 7/1986 | Naples et al. |
| 2010/0233226 A1 | 9/2010 | Ferain et al. |

(Continued)

OTHER PUBLICATIONS

Int'l. Search Report for PCT/EP2018/082703, dated Jan. 28, 2019.

*Primary Examiner* — Rex R Holmes
(74) *Attorney, Agent, or Firm* — Blue Filament Law PLLC

(57) ABSTRACT

An implantable cuff electrode and/or optrode (40) adapted to encircle a substantially cylindrical tissue (70), is provided that includes a support sheet (43) rolled about a longitudinal axis, forming a cuff of inner diameter, Dc, and extending over a length, L a central portion, extending over a length, lc, of at least 50% of the length, L, and having a mean central thickness, tc, and wherein the central portion is flanked on either side by, a first edge portion (43e) of mean edge thickness, te1, and a second edge portion (43e) of mean edge thickness, te2, at least a first electrode contact or a first optrode exposed at an inner surface of the cuff, and remote from an outer surface forming the exterior of the cuff, Characterized in that, the mean edge thicknesses, te1, te2, of the first and second edge portions are each lower than tc.

15 Claims, 12 Drawing Sheets

(51) Int. Cl.
*A61N 5/06* (2006.01)
*B32B 38/00* (2006.01)
*A61N 5/067* (2006.01)

(52) U.S. Cl.
CPC .......... *B32B 38/0012* (2013.01); *A61N 5/067* (2021.08); *A61N 2005/063* (2013.01); *A61N 2005/0651* (2013.01); *A61N 2005/0659* (2013.01); *B32B 2535/00* (2013.01)

(58) Field of Classification Search
CPC .... A61N 2005/0651; A61N 2005/0659; A61N 2005/067; A61N 1/0551; A61N 1/375; B32B 38/0012; B32B 2535/00
See application file for complete search history.

(56) References Cited

U.S. PATENT DOCUMENTS

| | | | |
|---|---|---|---|
| 2014/0188202 A1* | 7/2014 | Zarembo | A61N 1/0556 607/118 |
| 2015/0174396 A1 | 6/2015 | Fisher et al. | |
| 2015/0374975 A1 | 12/2015 | Callegari et al. | |
| 2016/0263376 A1 | 9/2016 | Yoo et al. | |
| 2017/0080244 A1 | 3/2017 | Chiel et al. | |
| 2017/0246453 A1 | 8/2017 | Fisher et al. | |
| 2017/0304614 A1 | 10/2017 | Yoo et al. | |

* cited by examiner

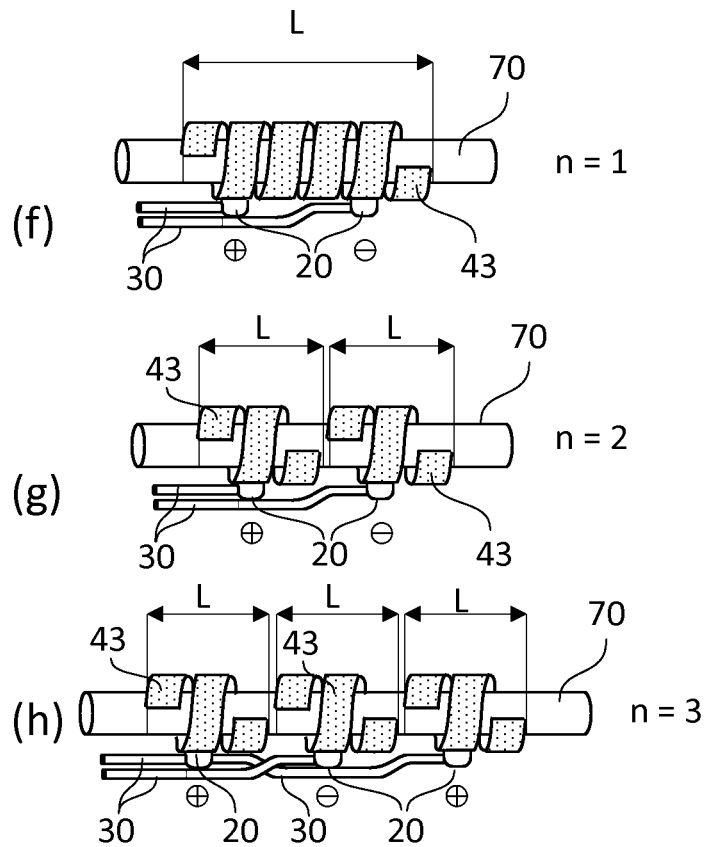
FIG.3 (contd)
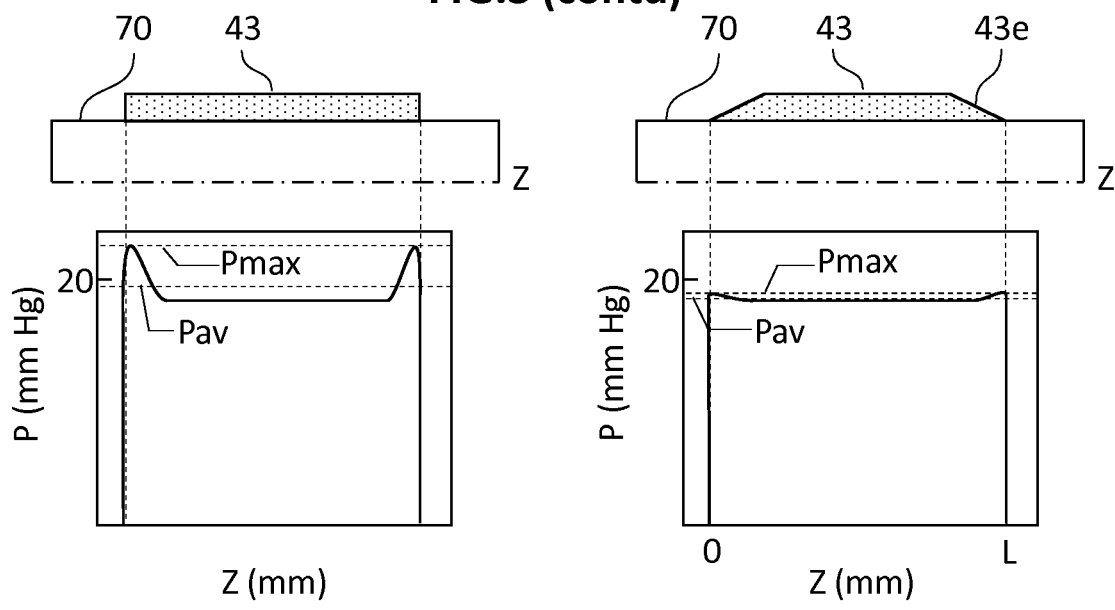
FIG.4

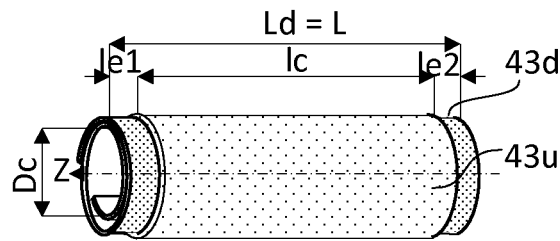
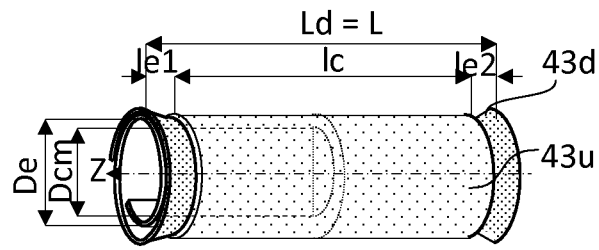
FIG.10(a) (INV)       FIG.10(b) (P.A.)
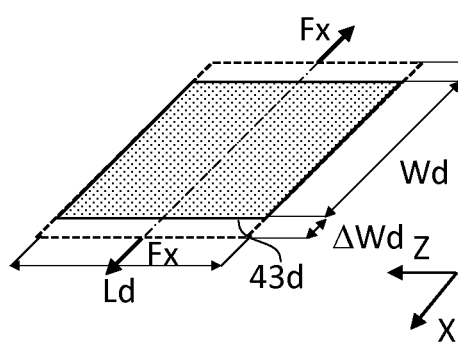
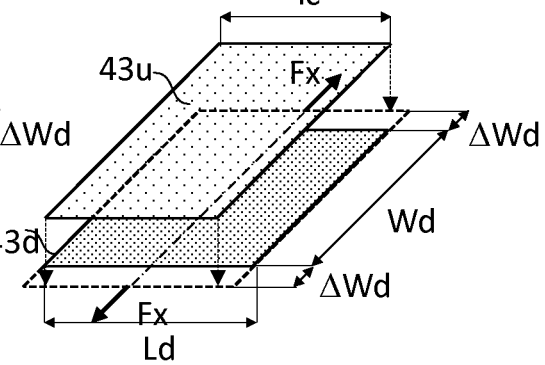
FIG.11(a1)      FIG.11(a2)
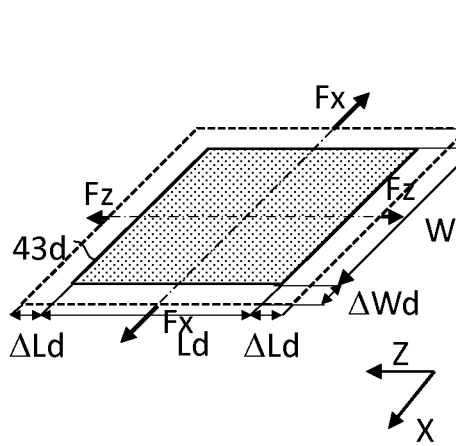
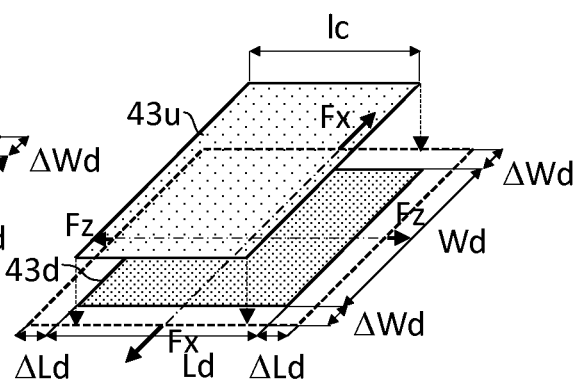
FIG.11(b1)      FIG.11(b2)

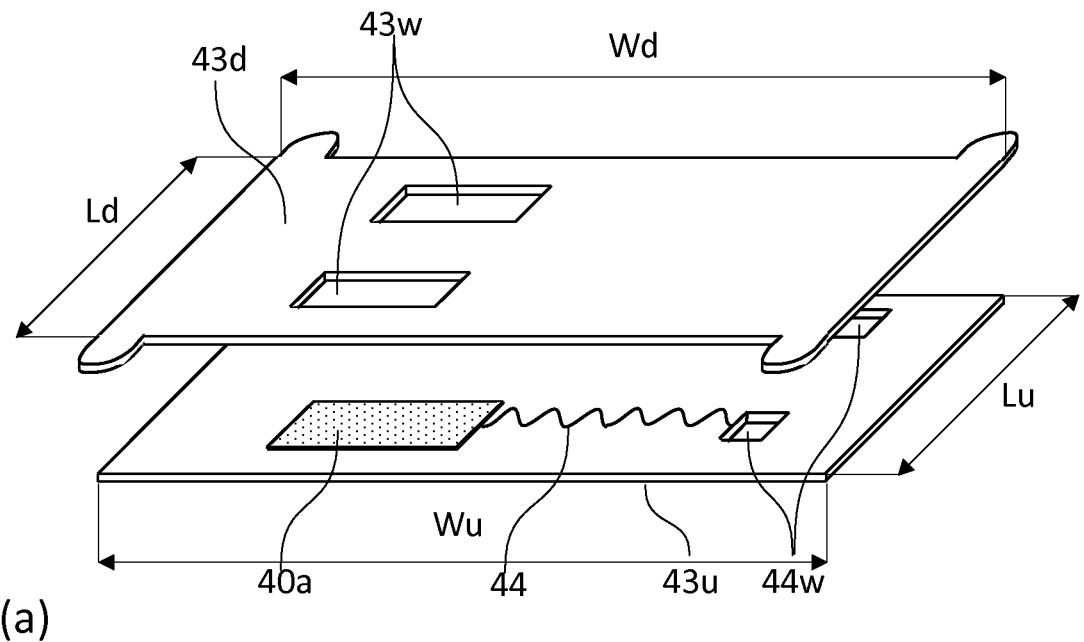
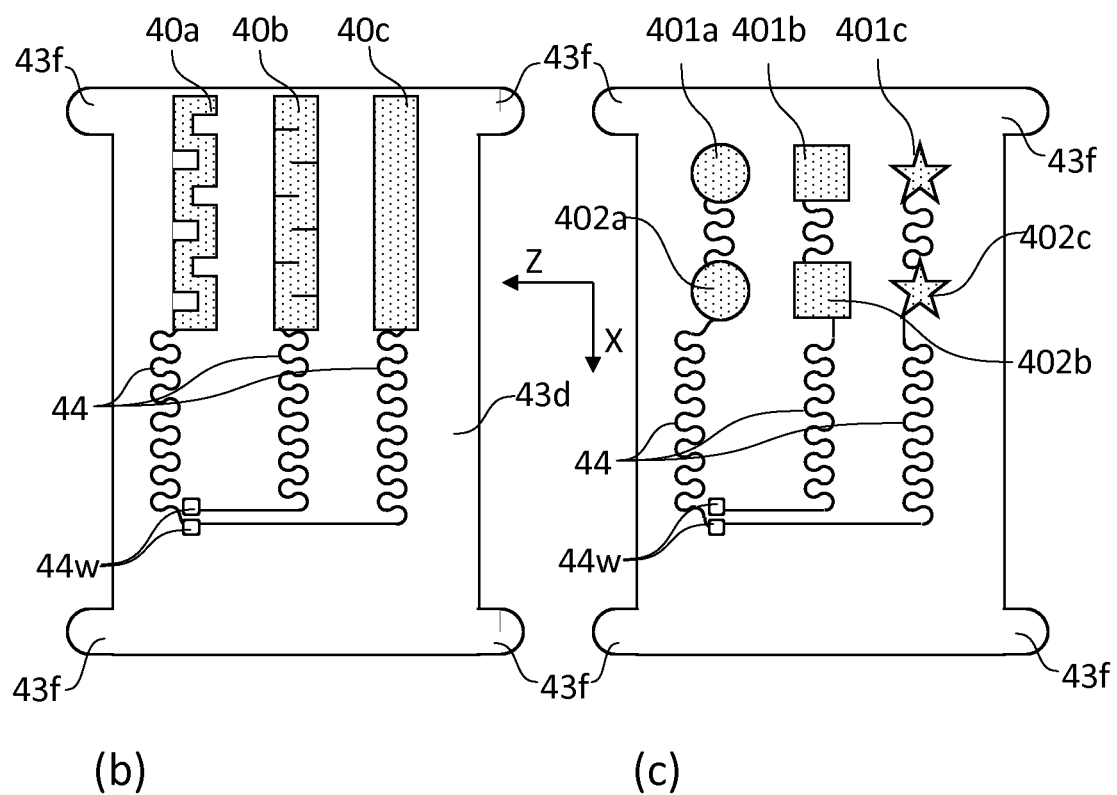
FIG.12

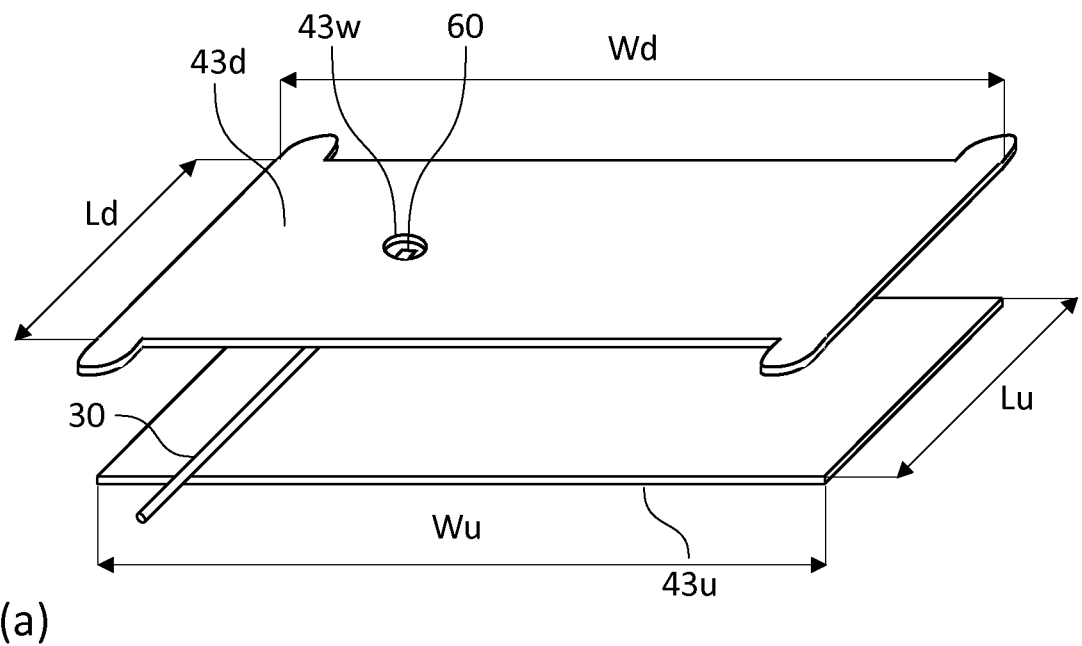
(a)
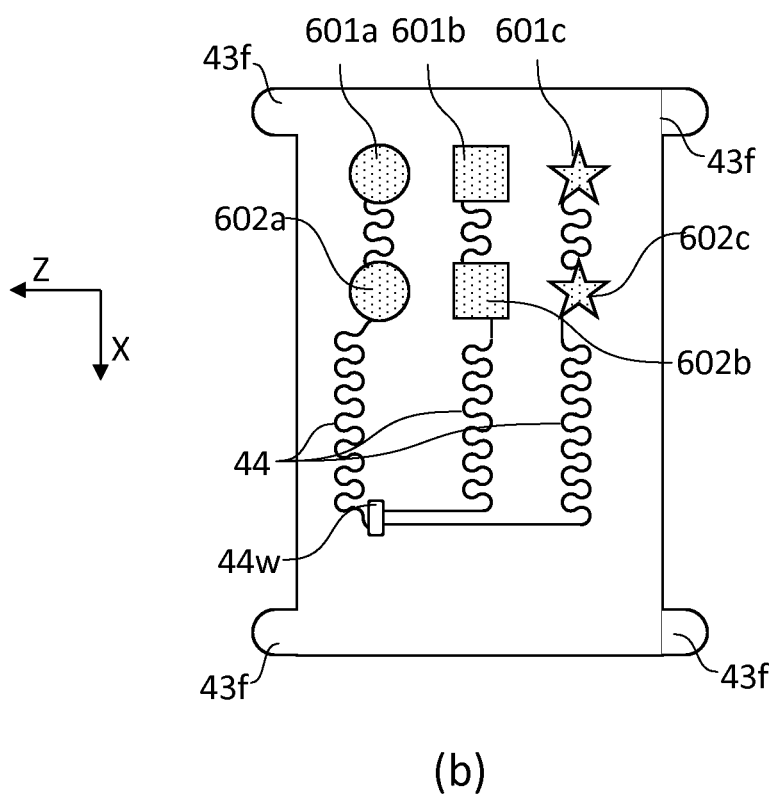
(b)
FIG.13

US 11,318,301 B2

CUFF ELECTRODE OR OPTRODE COMPRISING SOFT EDGES AND PROCESS FOR THE PRODUCTION THEREOF

TECHNICAL FIELD

The present invention is in the field of implantable medical devices (IMD) for use in medical treatments involving the transmission of electrical pulses or light pulses between the IMD and a biological tissue. In particular, it concerns a novel concept of cuff electrodes or optrodes for coupling to a nerve or other substantially cylindrical tissue by wrapping around the nerve or tissue, which has several advantages over state of the art cuff electrodes and optrodes, including being less traumatic or damaging to the nerve or tissue the cuff electrode or optrode is coupled to and, for cuff electrodes, reduction of electrical power losses and of formation of stray currents, and the like. These advantages can be achieved without increasing the production costs of the cuff electrode compared with state of the art cuff electrodes.

BACKGROUND OF THE INVENTION

Implantable medical devices (IMD) have been used for decades for treating a number of disorders, in particular neurological disorders. A major type of IMD's consists of neurostimulators, which deliver electrical pulses to a tissue such as a nerve or a muscle for diagnosing or treating a number of disorders such as Parkinson's disease, epilepsy, chronic pain, motor disorders, and many other applications. In recent years, treatment of tissues with optical energy has shown encouraging potential for the treatment of disorders, either to support the field of optogenetics or using direct infrared light. As illustrated in FIG. 1, in its simplest form, a device for delivering electrical pulses comprises an energy pulse generator lodged in a housing (50), stimulating electrode contacts (40a, 40b), and leads (30) coupling the electrode contacts to the energy pulse generator to transmit energy from the energy pulse generator to the electrode (40) in the form of electrical energy. The energy pulse generator can generate electrical pulses transmitted to the electrode contacts by conductive leads. Alternatively, and as described, e.g., in EP3113838B1, the energy pulse generator can generate light transmitted through fibre optics to photovoltaic cells which transform the light energy into electrical energy which is fed to the electrode contacts. The term "lead" is herein used to define both electric conductors (e.g., wires, tapes) and fibre optics.

For light treatment of a tissue, a so-called optrode can be used. An optrode can be a light emitter focusing a light beam onto a precise area of a tissue, or it can be a light sensor, sensing a reflected, transmitted, or scattered light beam emitted by a light emitter. A light emitter can be in the form of a bevelled edge fibre optic or of a fibre optic coupled to a lens, focusing a light beam on a precise area of a tissue to be treated. Alternatively, the light emitter can be one or more light emitting sources, such as a light emitting diode (LED), a vertical-cavity surface-emitting laser (VCSEL), or another type of laser diode. The light emitting source can be powered by electric current in a similar way to the electrodes discussed supra.

In many applications, the electrodes or optrodes must be applied directly onto the tissue to be treated, requiring the use of an implantable device. For tissues having a substantially cylindrical configuration, cuff electrodes and/or optrodes (40) are generally used to wrap around the cylindrical tissue, such as nerves, muscular tissues, and any tissue in the shape of elongated strands or trunks. A cuff electrode comprises, on the one hand, an electrically insulating support (43) comprising a sheet forming a hollow tubular support, of generally cylindrical geometry; and, on the other hand, at least one electrode contact (40a, 40b) or an optical contact (60) exposed at an inner surface of the electrically insulating support, so that it is in electrical and/or optical contact with the tissue the cuff is wrapped around. The at least one electrical contact or optical contact is activated by the energy pulse generator as described above. US2017304614 and US2016263376 describe cuff electrodes and their uses, without defining any specific geometry of the cuff electrodes. US20170246453 describes a cuff electrode for achieving block of an action potential in a large diameter nerve. US20150174396 describes a cuff formed by two relatively stiff portions coupled to one another by an elastic portion allowing the clamping of a nerve between the two relatively stiff portion in the manner of a book.

Three main families of cuffs are available on the market, illustrated in FIG. 3:

Self-curling cuff (cf. FIG. 3(a)-(c)), wherein the electrically insulating support is made of a resilient material which is biased to spontaneously curl up around a cylindrical tissue. Self-curling cuff electrodes are particularly advantageous because their inner diameter, Dc, can vary depending on the diameter of the tissue they are wrapped around, or on variations of the diameter of the cylindrical tissue, following e.g., post-surgical inflammation or the like. Self-curling cuff electrodes are described e.g., in U.S. Pat. No. 4,602,624.

Split-cylinder cuff (cf. FIG. 3(d)&(e)), wherein the electrically insulating support forms a cylinder with an open slit allowing insertion thereof over a cylindrical tissue. The slit is then closed. The cuff electrode is either provided with self-locking means or can be closed with external means, such as by ligaturing and the like. A flap may cover the slit. One drawback of slit cylinder cuff electrodes is that, once the slit is closed, the inner diameter thereof cannot vary anymore. Examples of slit cylinder cuff electrodes can be found e.g., in U.S. Pat. No. 8,155,757.

Helical cuff (cf. FIG. 3(f)-(h)), wherein the electrically insulating support forms a helix wrapped around the cylindrical tissue. This geometry is very versatile, and several short helical cuff can be positioned side by side at different distances, and their inner diameter can follow variations of the tissue diameter. Examples of helical cuff electrodes can be found e.g., in U.S. Pat. No. 5,964,702 or U.S. Pat. No. 8,478,428, and they are briefly discussed in [0004] of US2010233266.

One major issue with cuff electrodes is compression generated tissue injuries. For example, in nerves, such injuries produced by the pressure applied onto the nerve by the cuff electrode may induce nerve blood flow impairment, epineurial and endoneurial oedema, demyelination, and axonal degeneration. A mean pressure not exceeding 20 mm Hg is generally considered as agreeable in the art. The mean value of the pressure, however, does not take account of pressure peaks at the free edges of the cuff electrode, where stresses are concentrated. As illustrated in FIG. 4(a), pressure exerted on a tissue is particularly acute at the edges of the cuff, in particular during movements. FIG. 5 illustrates several cuff edge geometries attempting to reduce the stress concentration at the edges of electrode cuffs. FIG. 5(a) shows a traditional straight edge cuff, yielding a pressure profile as illustrated in FIG. 4(a). FIG. 5(b) shows a geometry forming a funnel driving towards the interface between the cuff and the tissue it is wrapped around. The edges of the sheet are bevelled such that the inner surface is smaller than the outer surface. This solution is discussed in US20150374975. It is not clear that the pressure at the edges is lower than in the cuff of FIG. 5(a), but it is clear that the funnel shaped edges facilitate penetration of body fluids between the cuff and the tissue. FIG. 5(c) shows a cuff with rounded edges. This geometry probably reduces somewhat the pressure at the edges, but it also forms a funnel enhancing penetration of fluids between electrode and tissue and thus provoking charge losses. Such geometry is also more complex to produce. Finally, FIG. 5(d) shows a cuff with trumpet shaped edges. Again, pressure is clearly reduced at the edges, but the edges form a funnel having the same drawbacks as the geometries illustrated in FIG. 5(b)&(c) discussed supra. Another issue with edges forming a funnel is that the electrode contact must be positioned at a distance, d1, from the edges which is larger than for a straight edge electrode cuff as illustrated in FIG. 5(a), thus increasing the overall length, L, of the cuff electrode.

The efficacy of a cuff electrode is impaired by the formation at the edges of the cuff of a so-called virtual electrodes appearing in the absence of an actual electrode contact. A virtual electrode is formed when the activating function, which indicates the probability for a substantially cylindrical tissue to be activated at one point, reaches a certain value. The activating function is proportional to the second derivative of the voltage profile along the cylindrical tissue. As the cuff support is electrically insulating, the voltage profile varies sharply at the edges of the cuff, giving rise to a high value of the activating function at the level of the cuff's edges and thus a high probability for the nerve to be activated where it should not be and in an uncontrolled manner. The edges geometries of FIG. 5(b)&(c) do not reduce, and for FIG. 5(c) even increases the activating function at the edges. Only the trumpet edge geometry of FIG. 5(d) may reduce the value of the activated function at the cuff's edges.

It can be seen from the foregoing that numerous problems remain unsolved with to date cuff electrodes and optrodes. The present invention proposes a cuff electrode and/or optrode which substantially reduces both compression generated tissue injuries, reduces current losses, and the value of the activated function responsible for the formation of stray currents along a cylindrical tissue, outside of the area covered by the cuff electrode. These and other advantages are described in more details in the following sections.

SUMMARY OF THE INVENTION

The present invention is defined in the appended independent claims. Preferred embodiments are defined in the dependent claims. In particular, the present invention concerns an implantable cuff electrode and/or optrode adapted to encircle a substantially cylindrical tissue, and comprising:

a support sheet (43) which, when deployed on a flat surface, comprises first and second longitudinal edges extending parallel to a transverse axis, X, wherein the support sheet is non-conductive and is rolled about a longitudinal axis Z, normal to the transverse axis X, thus forming a cuff of substantially cylindrical or helical geometry defining a lumen extending over a length, L, along the longitudinal axis, Z, of substantially constant inner diameter, Dc, measured along a radial axis, R, normal to the longitudinal axis, Z, wherein said cuff comprises, an inner surface forming an interior of the cuff and defining a lumen, and an outer surface forming an exterior of the cuff, separated from the inner surface by a thickness of the cuff, a central portion, extending over a length, lc, of at least 50% of the length, L, of the cuff, and having a mean central thickness, tc, measured normal to the longitudinal axis, Z, and wherein the central portion is flanked on either side by, a first edge portion extending from a first free edge of the cuff to the central portion along the longitudinal axis, Z, and a second edge portion extending from a second free edge of the cuff to the central portion along the longitudinal axis, wherein the first free edge portion has a mean edge thickness, te1, and the second free edge portion has a mean edge thickness, te2, at least a first electrode contact made of a conductive material exposed at the inner surface of the cuff, and being remote from the outer surface forming the exterior of the cuff, and/or at least a first optical contact for guiding a light beam from the inner surface towards the longitudinal axis, Z, wherein, the mean edge thicknesses, te1, te2, of the first and second edge portions are each lower than the mean central thickness, tc, (te1<tc and te2<tc), and in that, the inner surface of the cuff extends beyond the central outer surface in both directions along the longitudinal axis, Z.

The first and second longitudinal edges are considered to be extending parallel to a transverse axis, X, if at least 80%, preferably at least 90% of a length of the first and second longitudinal edges are straight and parallel to the transverse axis, X. The presence of protrusions or recesses of small dimensions (extending over less than 20% of the lengths) do not make the edges non-parallel.

The implantable cuff electrode and/or optrode of the present invention can be a self-curling cuff, a split cylinder cuff, or a helical cuff. The support sheet when deployed on a flat surface can be rectangular.

In a preferred embodiment, the support sheet is formed of an outer sheet comprising the outer surface, adhered to an inner sheet comprising the inner surface wherein said inner sheet has the inner length, Ld, and said outer sheet has the outer length, Lu, and wherein the inner sheet extends beyond the outer sheet in both directions along the longitudinal axis, Z. The inner sheet alone defines the first and second longitudinal edges of the support sheet.

Alternatively, or concomitantly, when deployed on a flat surface, said first and second longitudinal edges are bevelled across the thickness, such that the outer surface has the outer length, Lu, and the inner surface has the inner length, Ld.

The cuff can form a self-curling cuff, wherein the support sheet is formed of an outer sheet comprising the outer surface, adhered to an inner sheet comprising the inner surface, and wherein said inner sheet is made of a resilient material and is resiliently pre-strained along a transverse axis, X, normal to the longitudinal axis, Z, to create a bias suitable for self-curling the support sheet about the longitudinal axis, Z, to resiliently form a substantially cylindrical self-curling cuff of inner diameter, Dc.

The length, lc, of the central portion is preferably at least 65%, more preferably at least 75% of the length, L, of the cuff, and is less than 95%, preferably less than 90%, more preferably less than 85% of the length, L, of the cuff. Alternatively, or additionally, the first and second edge portions have a length, le1, le2, respectively, measured along the longitudinal axis, Z, wherein each of le1 and let is at least equal to 0.5 mm, preferably at least 1.0 mm, more preferably at least 2.0 mm, and wherein each of le1 and let is not more than 5.0 mm, preferably not more than 4.0 mm, more preferably not more than 3.5 mm. When deployed on a flat surface,
  (a) the outer surface has an outer width, Wu, measured along the transverse axis, X, normal to the longitudinal axis, Z,
  (b) the inner surface has an inner width, Wd, measured along a transverse axis, X, normal to the longitudinal axis, Z,
wherein the inner width, Wd, is preferably substantially equal to the outer width, Wu (Wd≅Wu).

The implantable cuff electrode and/or optrode can form a self-curling cuff. The support sheet advantageously has a bias and inner and outer widths, Wd, Wu, such that the support sheet self-curls into the substantially cylindrical cuff of inner diameter, Dc, with N loops, with N being comprised between 1 and 3.5, preferably between 1.5 and 3.0, more preferably between 2.0 and 2.5.

In an alternative embodiment, the implantable cuff electrode and/or optrode can form a split cylinder cuff, wherein the inner and outer widths, Wd, Wu, of the support sheet are such that the support sheet forms the substantially cylindrical cuff of inner diameter, Dc, with N loops, with N being comprised between 0.7 and 1.2, preferably between 0.8 and 1.0.

In yet an alternative embodiment, the implantable cuff electrode and/or optrode can form a helical cuff, comprising n=1 to 3 support sheets, wherein each of the n support sheets has an inner and outer widths, Wd, Wu, such that each support sheet forms a helix of N coils, with N being comprised between 1 and 5, preferably between 1.5 and 3, more preferably between 2 and 2.5.

The implantable cuff electrode and/or optrode preferably comprises a first and a second electrode contacts to form a bipolar electrode, and preferably a third electrode contact to form a tripolar electrode. Tripolar electrodes eliminate the problem of virtual electrodes discussed in continuation. The first electrode contact and, each of the optionally second and third electrode contacts can be in the form of,
  continuous strips extending transverse to the longitudinal axis, Z, preferably parallel to the transverse axis, X, when the support sheet is deployed on a flat surface, at least along the portion of the inner surface forming the interior of the cuff, preferably in a straight line or forming a serpentine when projected on the plane (X, Z), or
  discrete electrode contact elements distributed transverse to the longitudinal axis, Z, preferably parallel to the transverse axis, X, when the support sheet is deployed on a flat surface, at least along the portion of the inner surface forming the interior of the cuff.

Additionally, or alternatively to the electrode contacts described supra, the implantable cuff electrode and/or optrode of the invention preferably comprises a first optical contact selected among a fibre optics, preferably comprising a cleaved end or coupled to a lens or mirror, or a light source including a LED, VCSEL, or other laser diode. The implantable cuff electrode and/or optrode preferably further comprises a light sensing unit for sensing light transmitted, reflected, and/or scattered from the light beam.

The present invention also concerns a process for producing an implantable self-curling cuff electrode and/or optrode as defined supra. The process comprises the following steps:

(a) Providing an outer sheet comprising the outer surface of length, Lu, measured along the longitudinal axis, Z, and of width, Wu, measured along a transverse axis, X, normal to the longitudinal axis, Z, and further comprising an interface surface separated from the outer surface by a thickness of the outer sheet,
  (b) Providing an inner sheet made of a resilient material, comprising the inner surface of length, Ld, measured along the longitudinal axis, Z, and of width, Ws, measured along the transverse axis, X, and further comprising an interface surface separated from the inner surface by a thickness of the inner sheet, the inner sheet further comprising at least one contact window (43w) bringing the inner surface in fluid communication with the interface surface,
  (c) Applying a conductive material or an optical contact between the outer sheet and the inner sheet,
  (d) Stretching the inner sheet along the transverse direction, X, to yield a pre-strained inner sheet, and optionally stretching the inner sheet also along the longitudinal direction, Z, to yield an inner sheet pre-strained biaxially,
  (e) Adhering the outer sheet to the pre-strained inner sheet, through their respective interface surfaces to form a support sheet having first and second longitudinal edges extending parallel to the transverse axis, X, and having a conductive material or an optrode sandwiched between the outer sheet and the inner sheet, in registry with the at least one contact window
  (f) Releasing the stretching of the inner sheet, and allowing the inner sheet to recover an equilibrium geometry, wherein the stretching and widths, Wu, Wd, have been selected to allow the support sheet to self-curl about the longitudinal axis, Z, resiliently forming a substantially cylindrical cuff defining a lumen extending over the length, L, along the longitudinal axis, Z, of substantially constant inner diameter, Dc, measured along a radial axis, R, normal to the longitudinal axis, Z, with N loops, N being comprised between 1.0 and 3.5, of inner diameter, Dc, with N loops, N being comprised between 1.0 and 3.5,
wherein, the length, Ld, of the inner surface is larger than the length, Lu, of the outer surface, and wherein, the inner surface extends beyond the outer surface in both directions along the longitudinal axis, Z.

The inner diameter, Dc, of the lumen is considered as being substantially constant, if a relative difference, (De−Dcm)/Dcm, of an edge inner diameter, De, measured at an edge of the cuff and a central lumen diameter, Dcm, measured at the centre of the lumen, is less than 5%, preferably less than 3%, more preferably less than 1%.

In a preferred embodiment, the inner sheet has a length measured along the longitudinal axis, Z, equal to or larger than the inner length, Ld. The outer sheet has a length measured along the longitudinal axis, Z, larger than the outer length, Lu. The support sheet obtained after step (f) comprises first and second longitudinal edges extending parallel to the transverse axis, X. The first and second longitudinal edges are cut across the thickness, t, of the support sheet to form bevelled edges such that the outer surface has the outer length, Lu, and the inner surface has the inner length, Ld. The first and second longitudinal edges can be cut by machining or, preferably, by laser cutting.

BRIEF DESCRIPTION OF THE FIGURES

For a fuller understanding of the nature of the present invention, reference is made to the following detailed description taken in conjunction with the accompanying drawings in which:

FIGS. 4(a)-4(b) show the pressure profile applied by a cuff electrode to a nerve around which it is wrapped FIG. 4(a) straight edged cuff according to the state of the art, FIG. 4(b) cuff electrode according to the present invention.

FIGS. 10(a)-10(b) show examples of self-curling electrode, FIG. 10(a) according to the present invention, which can be formed by pre-stretching the inner sheet as illustrated in FIG. 11, and FIG. 10(b) according to the prior art, with a trumpet configuration.

FIGS. 11(a1), 11(a2), 11(b1), and 11(b2) show two embodiments for forming a self-curling cuff electrode as illustrated in FIG. 10, by FIGS. 11(a1)&(a2) unidirectional pre-stretching the inner sheet along the transverse axis, X, and FIGS. 11(b1)&(b2) bidirectional pre-stretching the inner sheet along the transverse axis, X, and along the longitudinal axis, Z.

FIGS. 12(a)-12(c) show: FIG. 12(a) an exploded view of a stretched cuff electrode comprising a two-layer laminated insulating support, with electrode contacts sandwiched between an inner layer and an outer layer, FIG. 12(b) cuff electrode comprising serpentine shaped electrode contacts, and FIG. 12(c) cuff electrode comprising discrete electrode contacts.

FIGS. 13(a)-13(b) show: FIG. 13(a) an exploded view of a stretched cuff optrode comprising a two-layer laminated insulating support, with a bevelled fibre optic sandwiched between an inner layer and an outer layer, FIG. 13(b) cuff optrode comprising several light emitting sources with serpentine conductive tracks for connexion to an electric source.

FIG. 14(a) cuff electrode, FIG. 14(b) cuff electrode with electrical sensing, FIG. 14(c) cuff optrode with bevelled fibre optic, FIG. 14(d) cuff optrode with optical sensing, FIG. 14(e) optrode with electrical sensing.

DETAILED DESCRIPTION OF THE INVENTION

Figure 1:
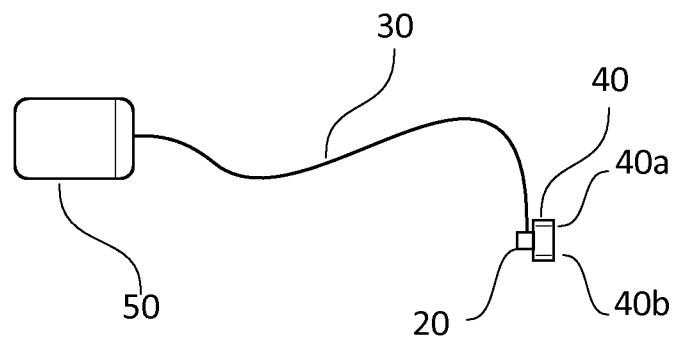
FIG. 1: shows an IMD according to the present invention.
Figure 2:
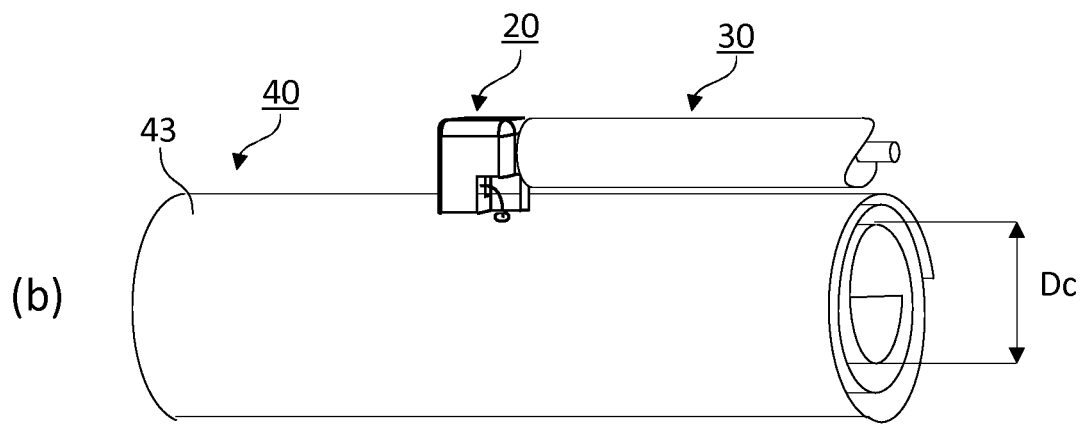
FIG. 2: shows an example of self-curling cuff electrode.

As illustrated in FIG. 1, an implantable cuff electrode and/or optrode according to the present invention is designed for use with an implantable medical device (IMD) comprising a housing (50) containing the electronics for controlling the functions of the IMD, including for example a source of power generally in the form of a primary or rechargeable battery, and an energy pulse generator, which can include an electrical pulse generator or a light emitting source. Because the housing (50) is usually too bulky to be implanted adjacent to the tissue to be treated, it is generally implanted in an easy to access region, remote from the tissue to be treated and from the cuff electrode/optrode. The cuff electrode/optrode (40) is therefore coupled to the housing by a lead (30) suitable for transporting the energy generated by the energy pulse generator to the electrode contacts (40a-c) or to the optrode of the cuff electrode/optrode. The energy is delivered in the form of electric energy to electrode contacts and to light emitting sources, such as LED's or VCSEL's, or in the form of light energy to a bevelled fibre optic or to a fibre optic coupled to a micro-optic device, such as a lens, a mirror, etc. The lead may consist of conductive leads, for use with an electrical pulse generator, conducting the electrical pulses from the generator directly to the electrode contacts or light emitting sources, without any transformation of the energy. An IMD of this kind is described e.g., in WO2009046764. Alternatively, the leads may comprise fibre optics for use with a light emitting source such as a LED. The optical energy is transported to a photovoltaic cell located adjacent to the cuff electrode/optrode, for conversion of the optical energy into electrical energy. An IMD of this kind which is suitable for use with a cuff electrode of the present invention is described e.g., in WO2016131492. Both energy transfer systems are known in the art and a person of ordinary skill in the art knows the pros and cons of each system. The present invention is not restricted to any particular energy transfer system type. The use of fibre optics with photovoltaic cells is, however, preferred for the numerous advantages it has over the use of electrical wires, such as the lack of interaction with magnetic fields encountered e.g., in magnetic resonance imaging (MRI) or in security portals at airports and the like.

As shown in FIGS. 3(a)-3(h) and 14(a)-14(e), a cuff electrode/optrode according to the present invention comprises an electrically non-conductive support sheet (43) in the form of a tubular cuff structure defining a lumen of inner diameter, Dc, formed by an inner surface (43d) and comprising an outer surface (43u), and at least a first electrode contact (40a), generally two and even three electrode contacts (40b, 40c) exposed at the inner surface of the cuff. Alternatively or concomitantly, the tubular cuff structure comprises at least a first optical contact (60), preferably two or more optical contacts (601a-c, 602a-c) exposed at the inner surface of the cuff The inner diameter, Dc, depends on the dimensions of the substantially cylindrical tissue the cuff is to be wrapped around. The inner diameter, Dc, is preferably comprised between 0.5 and 5 mm, more preferably between 1 and 3.5 mm, most preferably between 2 and 3 mm. The inner diameter, Dc, of the self-curling cuff electrode/optrode is generally comprised between 80 and 95% of the substantially cylindrical tissue diameter, Dn, of the tissue to be treated. For split cylinder cuff electrodes/optrodes, the inner diameter, Dc, is generally equal to or slightly larger than the diameter, Dn. For example, Dc can be comprised between 100 and 110% of Dn. The various components of the cuff electrode/optrode of the present invention are described in continuation.

Electrically Insulating Supports (43)

The cuff electrode/optrode (40) comprises an electrically insulating support (43) for coupling the implantable electrode/optrode element to a cylindrical tissue, such as a nerve. The insulating support comprises an inner surface (43d), at least a part of which contacts the substantially cylindrical tissue around which it is wrapped, and further comprises an outer surface (43u) separated from the inner surface by a thickness of the insulating support. The insulating support is used for securing the electrode contacts (40a-c) or optical contacts (60) at their treatment positions in electrical/optical contact with the substantially cylindrical tissue to be treated for long term implantation. The insulating support also serves for confining the current as much as possible in a circuit including a first and a second electrode contacts (40a, 40b) and optionally a third electrode contact (40c) passing through the substantially cylindrical tissue located between said first and second electrode contacts.

The insulating support is made of a non-conductive material, preferably a polymer. If the insulating material must be deformed during implantation and for accommodating any body movement, for examples for self-curling cuff electrodes (cf. FIG. 3(a)-(c)) and, in some cases, for helical cuff electrodes (cf. FIG. 3(f)-(h)), it is preferably made of an elastomeric polymer, such as silicone, a polyimide or polyurethane elastomer, or any biocompatible elastomer. For other electrodes geometries, such as split cylinder cuff electrodes (cf. FIG. 3(d)&(e)), besides biocompatible elastomers, the insulating support can be made of a more rigid material such as for example polyurethane or an epoxy resin.

As shown in FIGS. 3(a)-3(h) and 6-13(b), the insulating support can consist of a sheet material that is rolled up about a longitudinal axis, Z, to form a tubular, substantially cylindrical or helical cuff structure of inner diameter, Dc, measured along a radial direction, R, normal to the longitudinal axis, Z, and extending over a length, L, along the longitudinal axis, Z. When deployed on a flat surface, the sheet comprises first and second longitudinal edges extending parallel to a transverse axis, X. The sheet is preferably quadrilateral, forming e.g., a rectangle, a square, a parallelogram or a trapezoid. Alternatively, the edges extending along the longitudinal axis, Z (normal to X), can be curved or jagged. The sheet is preferably rectangular. The tubular cuff structure comprises an inner surface (43d), at least a part of which forming an interior of the cuff, and an outer surface (43u) forming an exterior of the cuff, separated from the inner surface by a thickness of the cuff. At least a portion of the inner surface of the cuff is in contact with the tissue when the cuff electrode is implanted around a substantially cylindrical tissue (70) (a substantially cylindrical tissue is herein defined as a tissue in the form of an elongated fibre, strand, trunk, etc., such as nerves, which is substantially cylindrical or at least prismatic, and having a length to diameter aspect ratio of at least 3, preferably at least 5, more preferably at least 10).

A tubular cuff can be divided in a central portion extending along the longitudinal axis, Z, flanked on either side by a first and second edge portions (43e) including a first and second edges of the tubular cuff. The central portion extends over a length, lc, of at least 50% of the length, L, of the cuff. The cuff has at the central portion a mean central thickness, tc, measured normal to the longitudinal axis, Z. The mean central thickness, tc, is herein the average of the tubular wall thicknesses measured over the whole of the central portion, excluding any window or through hole present in the central portion. The central portion can in some embodiments as illustrated e.g., in FIGS. 6-12, be obvious, in that the central portion has for example a substantially constant thickness, and the edge portions have a suddenly (stepped geometry) or continuously (bevelled geometry) lower thickness. In cases where a central portion can clearly be distinguished from first and second edge portions (43e), the length, lc, of the central portion is preferably at least 65%, more preferably at least 75% of the length, L, of the cuff, and is less than 95%, preferably less than 90%, more preferably less than 85% of the length, L, of the cuff. Conversely or alternatively, the first and second edge portions preferably have a complementary length, le1, le2, respectively, measured along the longitudinal axis, Z, wherein each of le1 and let is at least equal to 0.5 mm, preferably at least 1.0 mm, more preferably at least 2.0 mm, and wherein each of le1 and let is not more than 5.0 mm, preferably not more than 4.0 mm, more preferably not more than 3.5 mm. The sum of the central length, lc, and the first and second edge lengths, le1, le2, corresponds to the total length, L, of the insulating support measured along the longitudinal axis, Z, (lc+le1+le2=L).

Absent an obvious boundary between the central portion and the edge portions, or in case of any doubt, the central portion is defined as covering a length, lc, equal to 60% of the cuff length, L, and the first and second edge portions are defined as covering a length, le1=le2 equal to 20% of the cuff length, L, on either side of the central portion (lc=0.6 L, and Le1=le2=0.2 L). If boundaries are, however, obviously and indisputably identifiable between the central portion and first and second edge portions, said obvious boundaries prevail over the foregoing rule of lc=0.6 L, and Le1=le2=0.2 L, which is to be used exclusively in case of doubt or dispute. For example, if the cross-section of the insulating support forms a trapezoid as in FIGS. 3(a)&(e) and 7 to 9, then the central portion is defined by the rectangle included in the trapezoid, and the first and second edge portions are formed by the triangles on either side of said rectangle, regardless of the proportions of lc and le1 & le2 with respect to the cuff length, L.

The first cuff edge portion (43e) extends from the first free edge of the cuff to the central portion along the longitudinal axis, Z, and has a mean edge thickness, te1. The second edge portion (43e) extends from the second free edge of the cuff to the central portion along the longitudinal axis, Z, and has a mean edge thickness, te2. Like for the central portion, a mean edge thickness, te1, te2, is herein the average of the thicknesses of the tubular walls measured over the whole of the first and second edge portions, respectively, excluding any window or through hole present in said edge portions.

The gist of the present invention is to soften the edge portions (43e) of the tubular cuff, by ensuring that the inner surface of the cuff extends beyond the central outer surface in both directions along the longitudinal axis, Z, and that the mean edge thicknesses, te1, te2, of the first and second edge portions are each lower than the mean central thickness, tc, (te1<tc and te2<tc). As illustrated in FIG. 4(b) showing the pressure profile along the longitudinal axis, Z, applied by a cuff electrode according to the present invention onto a substantially cylindrical tissue around which it is folded, the pressure applied by the soft edges of a cuff electrode according to the present invention onto the substantially cylindrical tissue is substantially lower than by straight edge cuff electrodes illustrated in FIG. 4(a). In order to observe a substantial lowering of the pressure applied by the edges of a cuff onto a nerve or other tissue, it is preferred that the mean edge thicknesses, te1, te2, be at least 25% lower than the mean central thickness (te1, te2<0.75 tc), more preferably at least 30% lower (te1, te2<0.70 tc), more preferably at least 45% lower (te1, te2<0.55 tc). There are several ways of obtaining such edge design.

If the insulating support is made of a resilient material, the tubular cuff can be unfolded and deployed on a flat surface; to yield a flat support sheet wherein, The outer surface has an outer length, Lu, measured along the longitudinal axis, Z, and an outer width, Wu, measured along the transverse axis, X, and The inner surface has an inner length, Ld, measured along the longitudinal axis, Z, and an inner width, Wd, measured along the transverse axis, X.

If the insulating support is too rigid to allow such deployment, the same exercise can be made theoretically, by performing a central cylindrical projection of the insulating support, yielding a representation of the flat support sheet described supra for resilient supports.

According to the present invention, the inner length, Ld, is greater than the outer length, Lu (i.e., Ld>Lu). The inner width, Wd, can be lower than, higher than, or equal to the outer width, Wu.

Three main types of insulating supports (43) are discussed more in detail in continuation: self-curling supports, split cylinder supports, and helical insulating supports.

Self-Curling Insulating Supports

As shown in FIGS. 6-12(c), the sheet material can be made of a single layer or can consist of a laminate comprising an inner sheet comprising the inner surface (43d) and an outer sheet comprising the outer surface (43u) either adhered directly to one another thus forming a two-layer laminate, or to one or more core layers, thus forming a multi-layered laminate with more than two layers. Self-curling cuff electrodes must be biased so that the insulating sheet material spontaneously rolls up to form a tubular cuff structure. This can be achieved with a laminate comprising at least two layers. As shown in FIGS. 11(a1)&11(a2), the inner layer including the inner surface (43d) is pre-stretched along the transverse axis, X, by a deformation, 2 ΔWd, prior to and during adhesion thereof to the un-stretched outer layer including the outer surface (43u). When a laminate is formed, the force pre-stretching the inner layer is released, and the inner layer contracts back to its equilibrium dimension along the transverse axis, X, thus curling the sheet into a tubular cuff along the longitudinal axis, Z.

Because of the Poisson's ratio inherent to every material, which is the transverse to axial strain ratio of a material, by stretching the inner sheet along the transverse axis, X, the inner sheet contracts along the longitudinal axis, Z, to an extent depending on the level of transverse stretching and on the value of the Poisson ratio of the sheet material. Upon releasing the stress on the inner sheet to allow it to contract back to its equilibrium configuration along the transverse axis, X, the inner sheet also expands along the longitudinal axis, Z, and may thus form trumpet shaped cuff edges as illustrated in FIGS. 5(d) and 10(b), with an edge lumen inner diameter, De, measured at the edges, which is larger than the central lumen inner diameter, Dcm, measured at the centre of the lumen (De>Dcm). As illustrated in FIG. 10(b), the edges of a cuff are considered to be trumpet shaped, if the relative difference of lumen diameter, (De−Dcm)/Dcm≥5%, wherein De is the edge lumen inner diameter measured at an edge of the cuff and Dcm is the central lumen inner diameter measured at the centre of the lumen. Trumpet shaped cuff edges are detrimental to a good contact between the tissue (70) and the electrode contacts (40a-c) and can be responsible for current losses which are detrimental to the efficacy of the cuff electrode. This can be obviated to a certain degree by increasing the distance, d1, d2, separating an electrode contact from a trumpet shaped edge, compared with the corresponding distance required in a straight edge cuff electrode. The cuff length along the longitudinal axis is thus increased, which is not desirable as it becomes more invasive and cumbersome to implant. To prevent trumpet edges from forming as the insulating support curls up to form a tubular cuff, it suffices as illustrated in FIGS. 11(b1) and 11(b2), to pre-stretch the inner sheet along the longitudinal axis, Z, too, by an amount, 2 ΔLd, corresponding to the product of the material's Poisson's ratio and the pre-stretching level, 2 ΔWd, of the inner sheet along the transverse axis, X. If some level of trumpet shaped edges were desired, a fraction only of the foregoing pre-stretching along the longitudinal axis, Z, could be applied instead.

Figure 6:
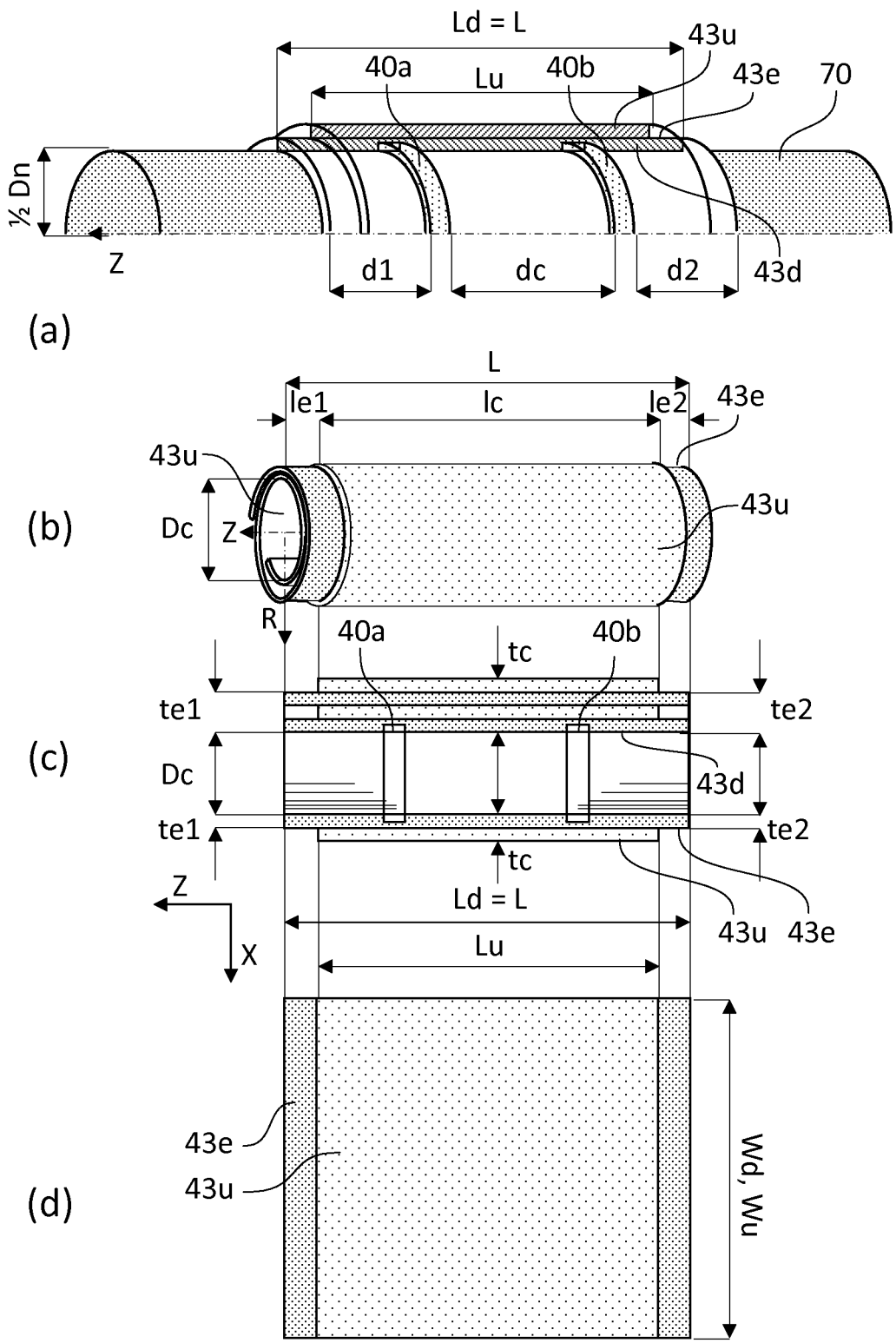
FIGS. 6(a)-6(d) show an embodiment of self-curling cuff electrode according to the present invention.

In a first embodiment illustrated in FIGS. 6 and 11, a two-layer laminate can be formed of an inner layer including the inner surface (43d) and an outer layer including the outer surface (43u) adhered to one another or to additional core layers sandwiched between the inner and outer sheets. The inner sheet has a length, Ld, measured along the longitudinal axis, Z, which is longer than the length, Lu, of the outer sheet (i.e., Ld>Lu), with the inner sheet extending beyond the outer sheet in both directions along the longitudinal axis, Z. Because this solution requires the use of a two-layer laminate, it is particularly suited, albeit not exclusively, for producing self-curling cuff electrodes, as depicted in FIG. 6. As explained supra, the inner sheet can be stretched along the transverse axis, X, prior to adhering it to the outer sheet and thus forming a self-curling support. To avoid formation of trumpet edges, the inner layer can also be stretched along the longitudinal direction, Z. Note that the insulating support sheet of the present embodiment can also be used for forming slit cylinder or helical cuff electrodes as discussed in continuation. A stepped edge can thus be formed by the outer layer being recessed with respect to the lower layer along said edge. The first and second edge portions (43e) have the thickness, te1, te2, of the inner layer or, for N>1 loop, having a thickness depending on the number N of loops. Even in the latter embodiment, a soft edge is obtained because, as shown in FIG. 6(c), even with two loops (see upper side of the Figure, the inner layer of the first loop in contact with the tissue is free to bend (upwards in the Figure) within the space between two loops, created by the recessed outer layer.

Figure 7:
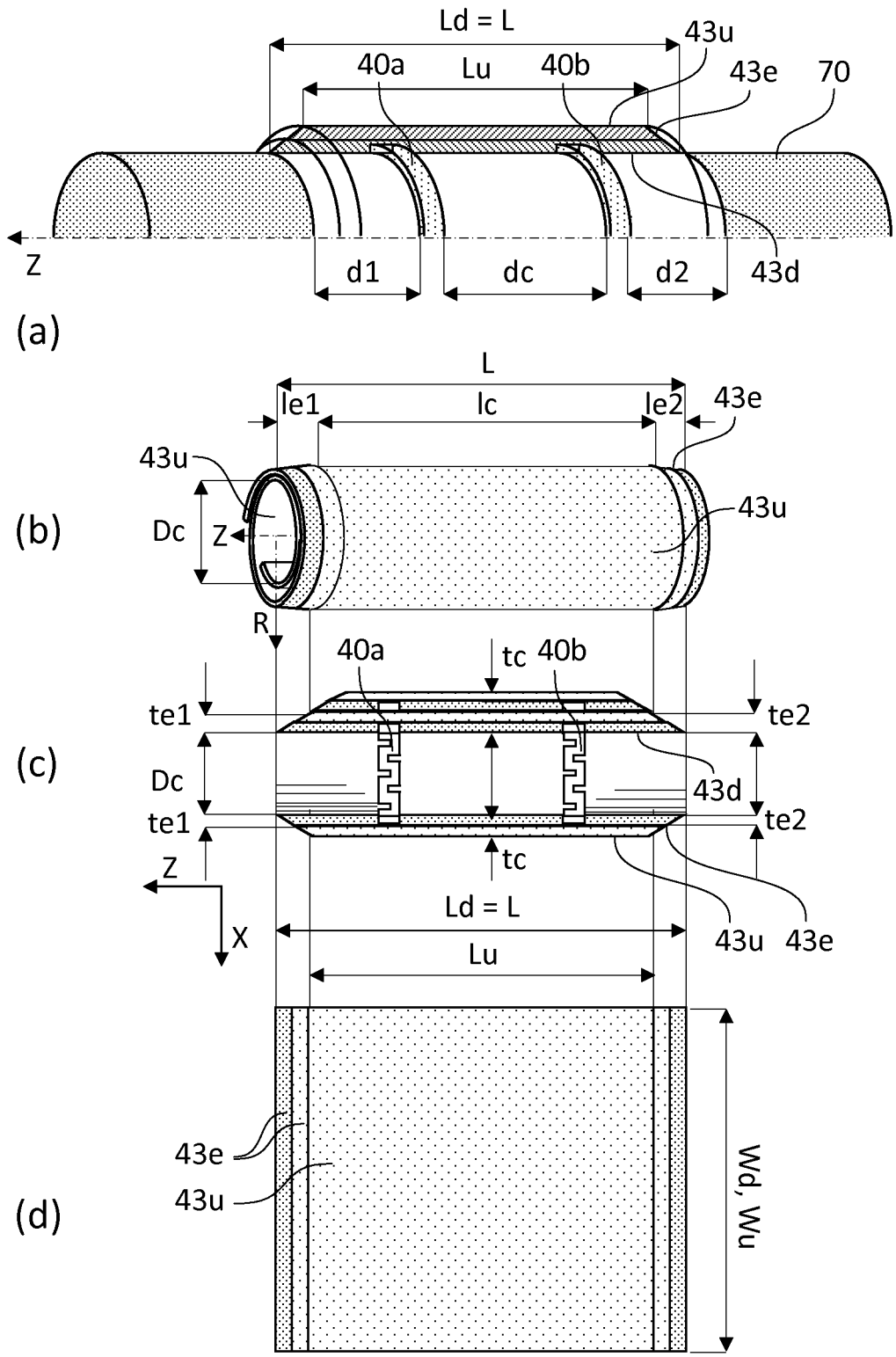
FIGS. 7(a)-7(d) show an alternative embodiment of self-curling cuff electrode according to the present invention.
Figure 8:
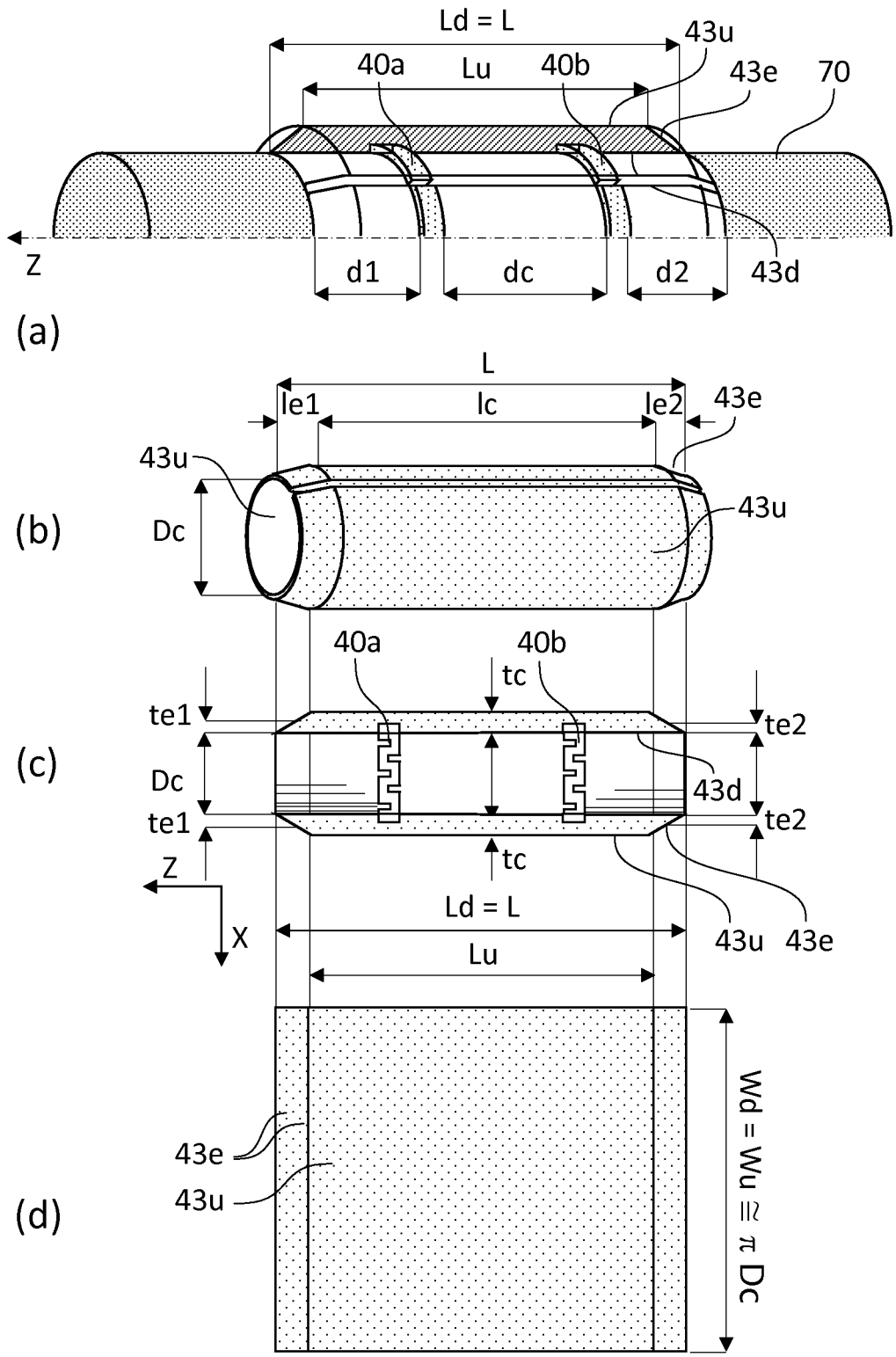
FIGS. 8(a)-8(d) show an embodiment of slit cylinder cuff electrode according to the present invention.
Figure 9:
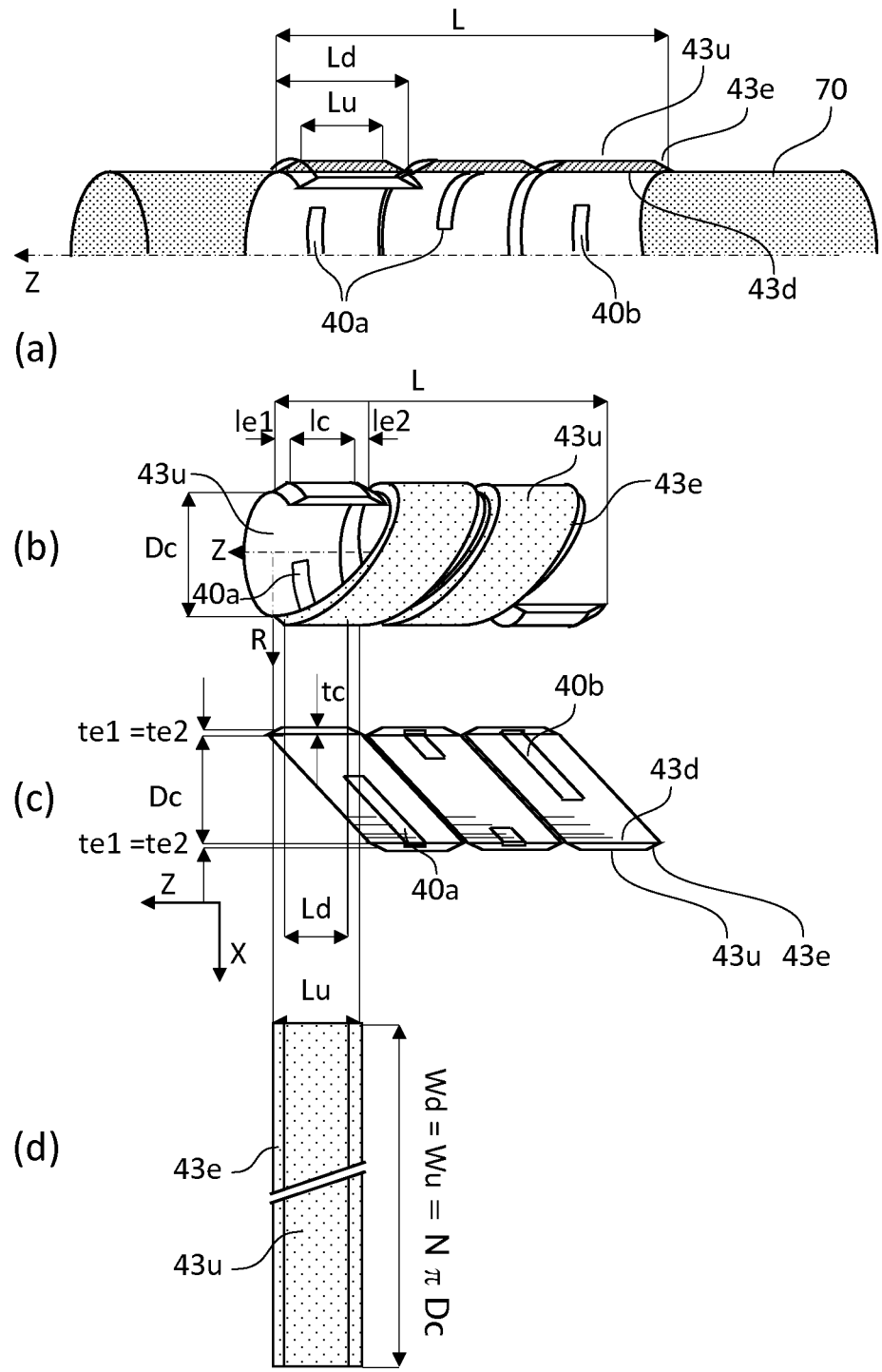
FIGS. 9(a)-9(d) show an embodiment of helical cuff electrode according to the present invention.

In an alternative embodiment illustrated in FIG. 7, the first and second edge portions can be bevelled, thus having a thickness decreasing from a maximum value of about tc where the first and second edge portions meet the central portion, down to or close to zero thickness at the first and second free edges. FIG. 7 shows a self-curling cuff electrode comprising a two-layer insulating sheet laminate with bevelled edges. The edge portions (43e) can be bevelled when deployed on a flat surface prior to allowing it to self-curl. The support sheet comprises first and second longitudinal edges extending parallel to the transverse axis, X, normal to the longitudinal axis, Z, said first and second longitudinal edges being bevelled across the thickness, such that the outer surface has the outer length, Lu, and the inner surface has the inner length, Ld. The support laminate with thus bevelled edge portions can be allowed to self-curl into a tubular cuff. As for the stepped-edge embodiment discussed with respect to FIG. 6, the thicknesses, te1, te2, of the edge portions (43e) depends locally on the number of loops. Alternatively, and as illustrated in FIG. 7(c), the edge portions can be bevelled after the insulating laminate is curled to form a tubular cuff. A continuously decreasing thickness from the boundary with the central portion to the first and second edges is thus obtained regardless of the local number of loops. Beveling of the edge portions can be performed with laser cutting techniques, well known in the art.

As illustrated in FIGS. 12&13, the insulating support of self-curling cuff electrodes may be provided with handling flaps (43f) protruding out of a perimeter of the support sheet. For examples, as shown in FIG. 12, in case of a quadrilateral sheet, four handling flaps can be positioned at each corner of the insulating support sheet (e.g., of the inner sheet) and protruding out along the longitudinal axis, Z. The handling flaps are useful to a surgeon for handling the self-curling cuff electrode as it is being implanted about a substantially cylindrical tissue (70). It is also possible to highlight the longitudinal edge of the insulating support sheet which is to be in contact with the tissue. Said edge is the edge parallel to the longitudinal axis, Z, which is adjacent to the one or more electrode contacts (40a-c) or to the one or more optical contacts (60). The highlight can be a coloured area, a coloured line, an arrow, or other graphical or alpha-numerical indication applied at or adjacent to said longitudinal edge. This simple solution ensures that a self-curling cuff electrode is not implanted the wrong way, with the risk that the one or more electrode contacts do not contact the tissue they are supposed to stimulate.

Figure 3:
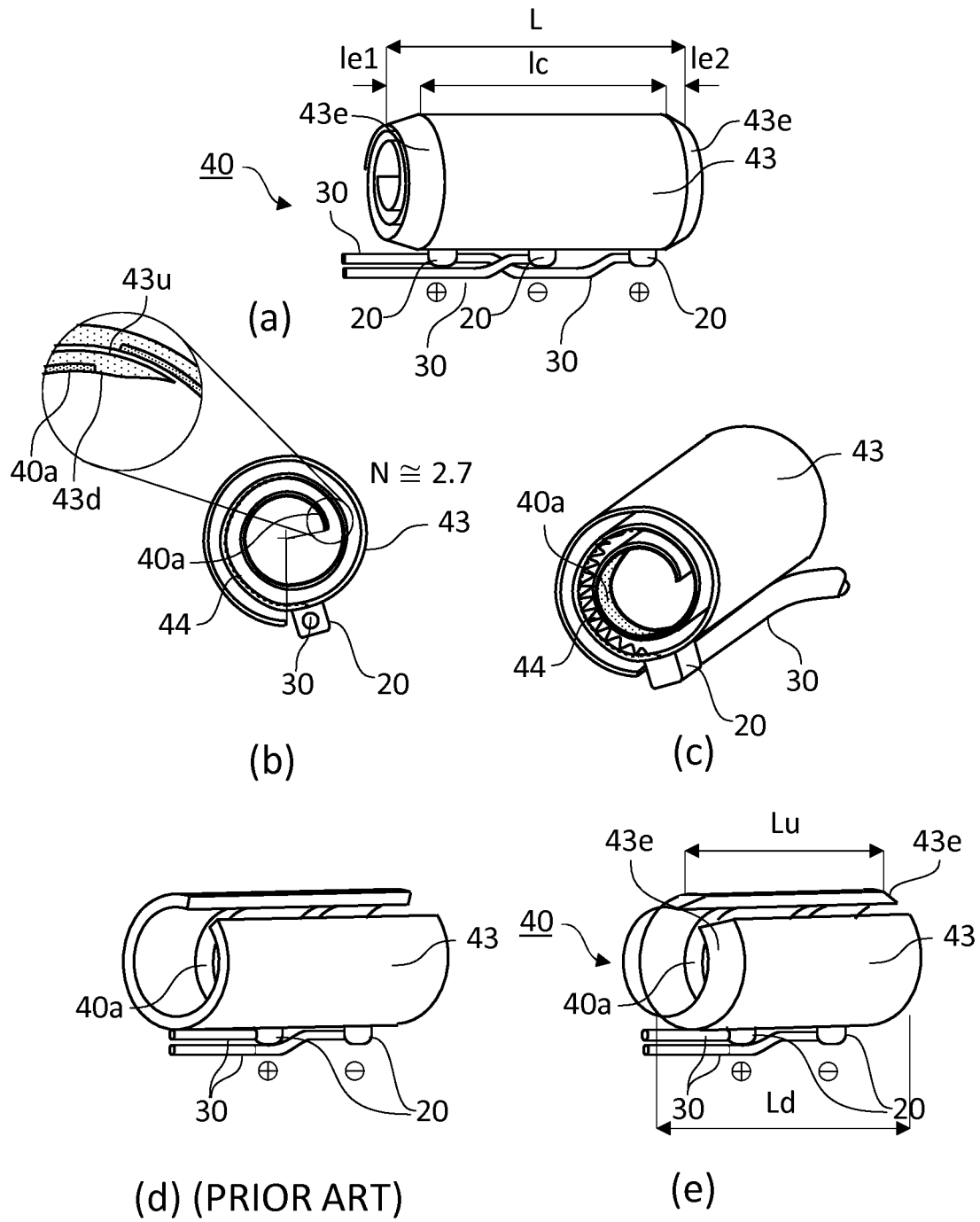
FIGS. 3(a)-3(h) show embodiments of cuff electrodes, FIGS. 3(a)-(c) perspective view, and (partial) cut views of self-curling electrodes according to the present invention, FIG. 3(d) split cylinder cuff electrode of the prior art, FIG. 3(e) split cylinder cuff electrode according to the present invention, FIGS. 3(f)-(h) helical cuff electrodes.

As shown in FIG. 3(a)-(c), a self-curling cuff electrode/ optrode generally surrounds a substantially cylindrical tissue with several loops. This has the double advantage of, on the one hand, safely securing the cuff electrode to the tissue and, on the other hand, to allow the self-curling cuff electrode to vary the inner diameter, Dc, thereof to the size of a specific tissue and, more important, to adapt to size variations of said tissue with time. The higher the number, N, of loops the self-curling cuff electrode surrounds the tissue with, the more secure is the coupling between the two. On the other hand, a high number, N, of loops increases the friction between adjacent loops, impairing the variations of the inner diameter, Dc, with tissue size variations and, at the same time increasing the bending stiffness of the cuff along the longitudinal axis, Z. It is preferred that the self-curling cuff electrode according to the present invention surrounds a substantially cylindrical tissue with a number N of loops comprised between 1 and 3.5, preferably between 1.5 and 3.0, more preferably between 2.0 and 2.5. In FIG. 3(b)&(c), self-curling cuff electrodes curled with a number N≅2.7 of loops are illustrated. The number, N, of loops formed by a self-curling cuff electrode depends on the actual diameter, Df, of the substantially cylindrical tissue which imposes the magnitude of the inner diameter, Dc, and on the widths, Wd, Wu, of the inner and outer surfaces, measured along the transverse axis, X. The level of bias obtained by pre-stretching the inner sheet prior to adhering it to the outer sheet determines the value of the inner diameter, Dc, the self-curling cuff electrode spontaneously reaches free of any external constraints. In general, it is accepted that Dc should be about 80 to 95%, preferably 85 to 90% of the diameter, Dn, of the cylindrical tissue, so as to ensure a constant compressive coupling between the tissue and the electrode contacts, without injuring the tissue.

As mentioned supra, for cuff electrodes in general, the inner width, Wd, can be larger than, smaller than, or equal to the outer width, Wu. In self-curling cuff electrodes, however, it can be advantageous if the inner width, Wd, is smaller than the outer width, such that the longitudinal edge portion, parallel to the longitudinal axis, Z, which contacts the substantially cylindrical tissue be bevelled. As illustrated in the inset of FIG. 3(b), the thus bevelled longitudinal edge portion smoothens the transition zone where the first loop ends, and the second loop starts and overlaps with the longitudinal edge portion. The bevelled longitudinal edge portion eliminates the sudden step which is formed with straight longitudinal edges, thus protecting the substantially cylindrical tissue from injuries.

Split Cylinder Insulating Supports

FIGS. 3(e) and 8(a)-8(d) illustrate split cylinder cuff electrodes. Though a multilayered laminate can be used as for self-curling cuff electrodes, a single layer support sheet can be used too and is illustrated in FIGS. 8(a)-8(d). The splits in FIGS. 3(e) and 8 are not covered by any flap to clarify the picture. A split cylinder cuff support can be moulded directly into its final geometry, with the first and second edge portions having their final mean thicknesses, te1, te2, smaller than the mean thickness, tc, of the central portion. Alternatively, it can also be made of an insulating support sheet which is folded to form a split cylinder as shown in FIG. 8, and set to this geometry, e.g., by cooling a thermoplastic material or setting a cross-linking thermoset or elastomer. The number, N, of loops is obviously lower than in self-curling cuff electrodes discussed supra, and can be comprised between 0.7 and 1.2, preferably between 0.8 and 1.0. For N<1, a flap (not shown) is generally provided to cover the open slit remaining after implantation. Again, the number, N, of loops depends on the diameter, Dn, of the cylindrical tissue, and on the widths, Wd, Wu, of the inner and outer surfaces measured along the transverse axis, X, when the support sheet is spread flat (or on a central cylindrical projection of the tubular support). The inner diameter, Dc, of split cylinder cuff electrodes should be at least 99%, preferably between 100 to 105% of the diameter, Dn, of the cylindrical tissue, to prevent injuries to the tissue caused by a generally more rigid insulating support than with self-curling cuff electrodes discussed supra.

As for self-curling cuff supports, the thinner edge portions can form a step-transition with the thicker central portion, by using a two-layer laminate formed of an inner layer including the inner surface (43d) and an outer layer including the outer surface (43u) adhered to one another or to additional core layers sandwiched between the inner and outer sheets. The inner sheet has a length, Ld, measured along the longitudinal axis, Z, which is longer than the length, Lu, of the outer sheet (i.e., Ld>Lu), with the inner sheet extending beyond the outer sheet in both directions along the longitudinal axis, Z, thus forming first and second stepped edges.

In an alternative embodiment illustrated in FIGS. 3(e) and 8(a)-8(d), the first and second edge portions (43e) can be bevelled from a thickness of about, tc, where they meet the central portion, down to, or close to a zero thickness at the free edges. The bevel can be formed in mould, or can be machined or laser cut in a second production step. In this embodiment, single- or multi-layered support sheets can be used.

Once implanted around a cylindrical tissue, the slit can be closed by any means known in the art, and the present invention is not restricted to any particular such means. For example, integrated locking means can be used or, more traditionally, the split can be ligatured. A person of ordinary skill in the art knows what technique is best suited to a particular application.

Helical Insulating Supports

Helical cuff electrodes are illustrated in FIGS. 3(f)-(h) and 9(a)-9(d). A helical cuff electrode can consist of n=1 or more helical units positioned side by side. FIG. 3(f)-(h) shows embodiments with n=1-3 helical units. The helical cuff electrode of FIG. 3(f) comprises n=1 helical unit, with two electrode contacts (not shown) connected to two corresponding leads (30). The helical cuff electrodes of FIG. 3(g)&(h) comprise n=2 and 3 helical units of length, L, respectively, each helical unit comprising a single electrode contact (not shown) connected to a corresponding lead (30), yielding n-contact cuff electrodes. This multi-unit construction has the advantage of allowing more spacing between contact electrodes with more flexibility for the tissue to bend between adjacent units. Each of the n helical unit forms a number, N, of coils about the longitudinal axis which is greater than or equal to unity (N=1). Preferably, the number, N, of coils formed by each helical unit is comprised between 1 and 5, preferably between 1.5 and 3, more preferably between 2 and 2.5. The number of coils depends on the number n of helical units, and on the number of electrode contacts in each helical unit. For n≥2 helical units, and for a total number of electrode contacts greater than 2, it is preferred that the electrode contacts be evenly distributed among the n helical units.

In one embodiment, only the two edge portions including a free edge of a helical cuff electrode (unit) are bevelled. In 9 FIGS. 9(a)-9(d), the edge portions are bevelled along the whole extent of the helix, including the edge portions of coils adjacent to a neighbouring coil. This embodiment is preferred because the edges of the helical cuff support are thus softer over their whole length in contact with the tissue (70). As shown in FIG. 9(d) a helical support can be produced from an elongated stripe of insulating material, which is folded to form a helix and set to freeze it in said geometry. The first and second edge portions (43e) of the elongated stripe can be produced directly with a mean edge thickness, te1, te2, which is lower than the mean central thickness, tc, of the central portion, e.g., by extrusion or moulding. Alternatively, a stepped edge as discussed supra with respect to self-curling and split cylinder cuffs can be formed by adhering together an inner sheet and an outer sheet, the former having a larger length, Ld, than the length, Lu, of the latter. The first and second edge portions can also be bevelled by machining or laser cutting. Some bias can be created yielding a certain level of self-curling by pre-stretching the inner sheet of a two- or more-layer laminate, as discussed supra in respect of self-curling cuff electrodes.

Electrode Contacts (40a-c)

The cuff electrode of the present invention further comprises at least a first electrode contact (40a), generally at least a second electrode contact (40b) and, in a preferred embodiment, at least a third electrode contact (40c), each electrode contact being exposed at the inner surface (43d) of the insulating support, such as to be in electrically conductive contact with the tissue the cuff electrode is wrapped around. The electrode contacts are also remote from the outer surface forming the exterior of the cuff. The at least one contact electrode is separated from the adjacent free edge of the insulating support by a distance, d1, d2. When the insulating support bears two electrode contacts (40a, 40b), they are separated from one another by a distance, dc. The distances, d1, d2, dc, must be determined to confine the current within the section of tissue comprised between the first and second electrode contacts, and to minimize current losses, straying beyond the boundaries of the cuff electrode. Several factors are responsible for current losses. First, conductive body fluids penetrating between the insulating support and the tissue are responsible for some current losses. Body fluid penetration is enhanced by a funnel shaped edge geometry of the insulating support, such as with trumpet edges or with bevelled edges inverted compared with the present invention, as illustrated in FIG. 5(d)&(b), respectively. With funnel shaped edges, the distances, d1, d2, separating an electrode contact from a free edge of the insulating support must be increased to minimize current losses. This is a drawback, as the overall length, L, of the cuff electrode is therefore increased. The edge design of a cuff electrode according to the present invention allows a tight contact between the insulating support and the tissue over the whole inner surface (43d), thus preventing excess penetration of body fluids between the insulating support and the tissue.

Figure 5:
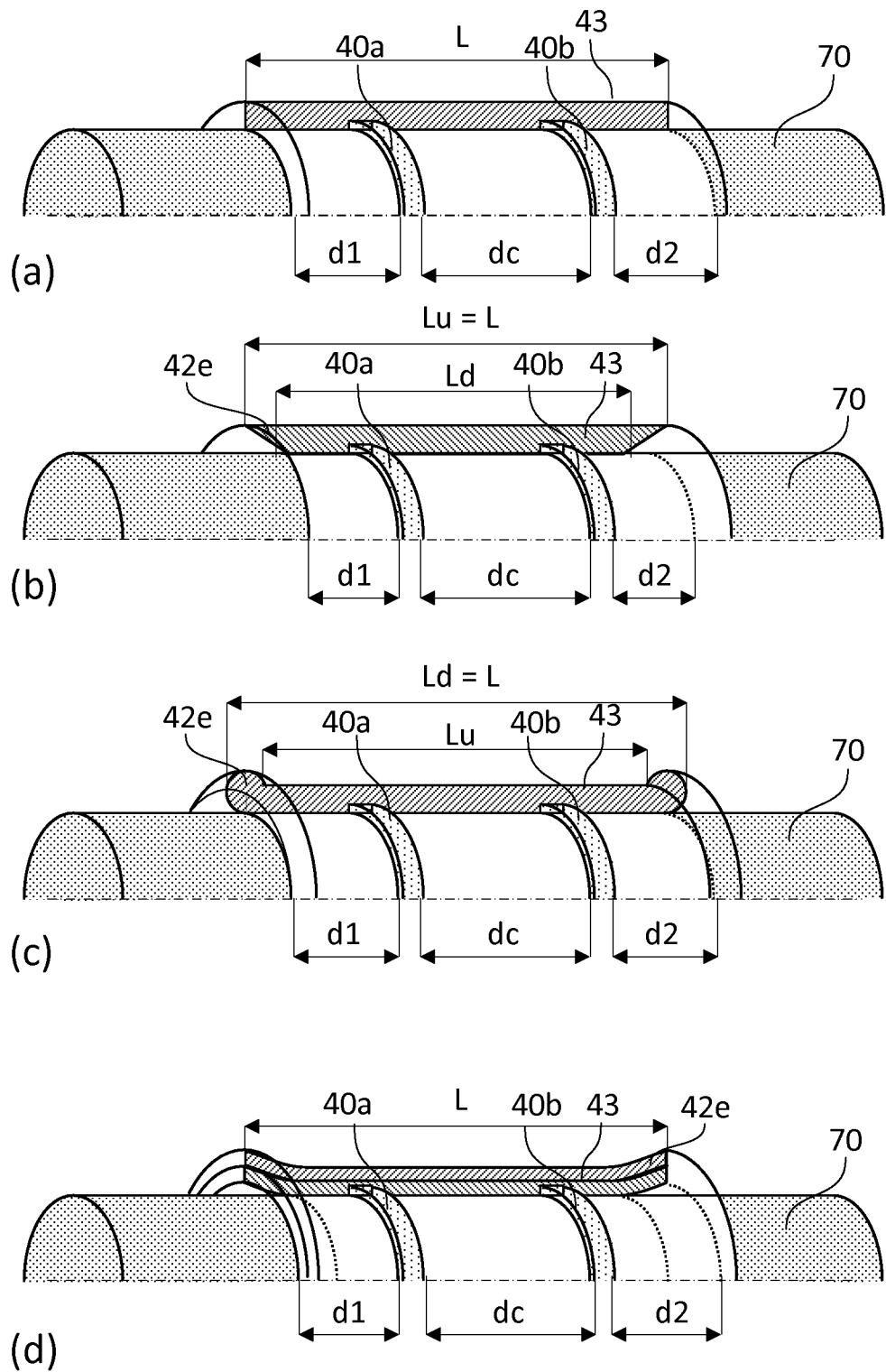
FIGS. 5(a)-5(d) show different cuffs edge geometries available on the market, FIG. 5(a) straight edges, FIG. 5(b) inversely chamfered funnel-shaped edges, FIG. 5(c) bead-edges, and FIG. 5(d) trumpet edges.

Undesired tissue stimulation can be observed in bipolar cuff electrodes. They can be caused by so called virtual electrodes formed at a section of the tissue located beyond a free edge of the insulating support. A circuit is thus created between such virtual electrode and an electrode contact adjacent to the free edge. The probability for a tissue to be activated by a stimulating current at any point along the substantially cylindrical tissue is proportional to the second derivative of the voltage profile along the substantially cylindrical tissue (=along the longitudinal axis, Z) and is characterized by the activating function. The value of the activation function is increased by sudden variations of the impedance and, conversely, is decreased in the absence of any such sudden variation. A virtual electrode can be formed beyond the free edges of a cuff electrode because there is a sudden variation of voltage at said free edges, between the insulating support and the conductive body fluids. The sharper the transition between the two media, the higher the value of the activation function. Referring to FIG. 5, it can be seen that straight edge cuff supports as illustrated in (a) create a sharp variation of impedance at the free edges. A bead edge illustrated in (c) is likely to create an even higher value of the activation function. By contrast, by decreasing the thicknesses, te1, te2, of the first and second edge portions from a value of about tc adjacent to the central portion, to a near to zero thickness at the free edges, the impedance decreases less sharply and the value of the activation function close to the free edges is decreased accordingly. The probability of a virtual electrode forming beyond the free edges of the cuff electrode is thus substantially reduced with the cuff electrodes of the present invention.

As shown in FIGS. 3(h) and 12(b)&(c), a cuff electrode according to the present invention may be tripolar, i.e., comprising three electrode contacts (40a-c) (in FIG. 3(h) the presence of the electrode contacts is indicated by the signs e, e). A tripolar cuff electrode can be advantageous over a bipolar cuff electrode (i.e., comprising two electrode contacts (40a, 40b)), in that the current is confined within the cuff, thus reducing current losses in the surrounding tissues and fluids. Tripolar cuff electrodes practically eliminate the formation of virtual electrodes discussed supra.

The electrode contacts (40a-c) are made of a conductive material, which must be biocompatible and long-term stable in a physiological environment. Typically, gold, platinum, iridium, and alloys thereof can be used for the electrode contacts. As shown in FIG. 12(b), the electrode contacts can be in the form of continuous stripes surrounding part or the whole of the circumference of the cylindrical tissue. The stripes extend transverse to the longitudinal axis, Z, preferably parallel to the transverse axis, X. If the insulating support is wrapped around the substantially cylindrical tissue with a number, N, of loops larger than 1, the length of the electrode contact stripes needs not be as long as the width, Wd, of the support sheet, measured along the transverse direction, X. The length of the electrode contact stripes does not need to exceed the circumference of the substantially cylindrical tissue of diameter, Dn, i.e. the conductive stripes need not be longer than π·Dn.

The electrode contacts can be printed or otherwise deposited (e.g., by physical vapour deposition (PVD) or by chemical vapour deposition (CVD)) onto the inner surface (43d) of the insulating support. This technique is advantageous in that the metal contacts do not stiffen the insulating support, which is particularly sensitive for self-curling and helical cuff electrodes comprising a resilient insulating support. Another advantage is that the electrode contacts are over the inner surface (43d) of the insulating support, thus ensuring a physical contact of the electrode contacts with the cylindrical tissue. The geometry of the electrode contacts can also be controlled very easily.

Alternatively, the electrode contacts can be coupled to the insulating support as metal stripes or elements. They can be coupled to the inner surface (43d) of the insulating support by gluing or welding. Alternatively, and as illustrated in FIG. 12(a), metal stripes can be sandwiched between an inner sheet and an outer sheet, forming a laminate. Contact windows (43w) are provided in the inner sheet to expose the metal surfaces to the inner surface (43d). The electrode contacts thus formed are recessed from the inner surface (43d) by the thickness of the inner sheet. As described in U.S. Pat. No. 8,155,757, recessed electrode surfaces provide an advantage in that they facilitate better cross-sectional current distribution across a nerve as well as more uniform charge injection into the tissue (e.g., a nerve) being stimulated. As shown in FIG. 6 of U.S. Pat. No. 8,155,757, the geometry of the edges of the contact windows (43w) can also be optimized depending on the desired charge distribution. This embodiment, requiring inner and outer sheets is well suited for producing self-curling cuff electrodes as discussed supra.

Because straight metal stripes cannot be stretched, thus impairing the advantage of self-curling and helical cuff electrodes of adapting to size variations of the tissue they are wrapped around, it can be advantageous to use stripes forming a serpentine, as shown in FIG. 12(b): electrode contacts (40a, 40b) instead of straight stripes as shown in FIG. 12(b): electrode contact (40c). As an alternative to continuous electrode contact stripes, discrete electrode contact elements (401a-c, 402a-c) can be used instead as illustrated in FIG. 12(c). The discrete electrode contact elements are preferably distributed in one or more rows extending transverse to the longitudinal axis, Z, more preferably parallel to the transverse axis, X, when the support sheet is deployed on a flat surface, at least along the portion of the inner surface forming the interior of the cuff. Discrete electrode contact elements can be advantageous over continuous electrode contact strips because they take full advantage of the flexibility of self-curling and helical insulating supports. Additionally, they may be used to stimulate specific points of a tissue.

If the electrode contacts are formed by sandwiching a metal stripe between inner and outer sheets as discussed above with reference to FIG. 12(a), the geometry of the individual electrode contacts is defined by the geometry of the contact windows (43w). The geometry of each discrete electrode is not restricted by the present invention. A person of ordinary skill in the art knows how to select the electrode contacts configuration and dimensions best suited for a particular application.

From the Electrode Contacts (40a-c) to the Corresponding Leads (30)

Energy pulses generated by the energy pulse generator located in the housing (50) are conveyed through the leads (30) and must be delivered to the electrode contacts in the form of electrical energy. As discussed supra, the electrode contacts are exposed at the inner surface (43d) of the insulating support, and remote from the outer surface (43u). The connexion between the electrode contacts and the leads is ensured by connecting pads (20) coupled to the outer surface of the insulating support. The connecting pads receive the one or more leads (30) and bring them in electrical communication with the corresponding electrode contacts. To this effect, the outer surface (43u) of the insulating support may comprise connecting windows (44w) allowing the formation of an electric communication between the electrode contacts (40a-c) and the electric pads (20) coupled to the outer surface.

If the connecting pads (20) are located in registry with the corresponding electrode contacts (40a-c), electrical communication between the leads and the electrode contact can be achieved directly though the connecting windows. If, on the other hand, the conductive pads are offset with respect to the electrode contacts, conductive tracks (44) can be used to bring in electrical communication the electrode contacts with the corresponding connecting pads. This is particularly the case with self-curling cuff electrodes which can be wrapped with N=2 or more loops, whilst the electrode contacts should only be long enough to contact the perimeter of the cylindrical tissues (i.e., one loop long). Conductive tracks (44) can be used to ensure electrical circuit continuity along the additional loops wherein the insulating support is not in contact with the cylindrical tissue. The conductive tracks can reach the outer surface through the connecting windows (44w).

In self-curling cuff electrodes forming a tubular cuff made of N loops, it is preferred that the connecting pads are coupled to a portion of the outer surface (43u) of the last loop, which forms an outer surface of the cuff. More preferably, the connecting pads are located as shown in FIG. 3(b)&(c), upstream and adjacent to the transverse free end forming the end of the last loop. In the present context, the term upstream refers to the winding direction starting from the interior of the cuff.

The conductive tracks consist of a continuous conductive path bringing the electrode contacts (40a-c) in electric communication with the connecting pads through the connecting windows (44w). If the insulating support is made of a resilient material, the conductive tracks preferably form a serpentine which can be stretched longitudinally. Like the electrode contacts, the conductive tracks can be printed or deposited onto the inner surface (43d) of the insulating support. Alternatively, they can be sandwiched between an inner layer and an outer layer as illustrated in FIG. 12(a). Since the conductive tracks need not be in contact with any external tissue, no contact window (43w) is required in the inner layer to expose the conductive tracks. The conductive tracks must, however, lead to a connecting window (44w) to establish an electric contact with the connecting pads coupled to the outer surface (43u).

In one embodiment, the energy pulse generator generates electrical pulses which are conducted to a connecting pad (20) coupled to the outer surface (43d) of the insulating support (43), by one or more conductive wires (30). The connecting pad (20) comprises a wire receiving portion for receiving the one or more conductive wires (30). It also comprises one or more electrode coupling surfaces in electrical contact with corresponding electrode contacts or with the one or more conductive tracks electrically coupled to corresponding electrode contacts. The connecting pad brings in electrical communication the one or more conductive wires (30) with corresponding electrode coupling surfaces or conductive tracks through the connecting windows (44w).

In an alternative embodiment, the energy pulse generator comprises a source of light emission and the lead (30) comprises fibre optics. Optical energy is transported to the connecting pads through the fibre optics. The connecting pad comprises a fibre optics receiving portion and contains a circuit including a photovoltaic cell for transforming the optical energy transported by the fibre optics into electrical energy to feed the electrode contacts, in a manner similar to the one described supra in relation with an electric pulse generator. A connecting pad for photovoltaic IMD's suitable for use with an electrode cuff according to the present invention is described in detail in PCT/EP2017/071858.

Optrodes (60)

As illustrated in FIGS. 14(a)-14(e), instead of, or additionally to electrode contacts, the insulating support sheet can be provided with one or more optical contacts. An optical contact as defined herein can be either a light emitter or a light sensor, or both. In some applications, stimulation of a tissue by light emission is mainly due to localized heating of the tissue. For such applications, it is preferred that the light directed by the optical contact be in the infrared range, preferably in the range of 750 to 3000 nm, more preferably of 1200 to 1800 nm. The cuff optrode of the present invention, however, can be used with light beams (60B) of any wavelength.

As illustrated in FIGS. 13(a)-13(b), an optical contact can be the end of a fibre optic, which is either bevelled or coupled to a lens, mirror, or other micro-optic device for directing and focusing a light beam (60B) towards a precise area of the tissue to be treated. The fibre optic can be coupled directly to the housing (50) and to the light pulse generator housed therein. Alternatively, a light emitting device located on an outer surface of the cuff can be electrically powered by the energy pulse generator located in the housing, and the fibre optic can be coupled to said light emitting device for guiding the light towards the tissue.

The optical contact (60) can also be a LED, a VCSEL or other laser diode (601a-c, 602a-c) which is mounted on the insulating sheet such as to be in direct optical contact with the tissue around which the cuff is wrapped. If the insulating sheet is transparent to the light wavelength emitted by the optical contact, then the light can be transmitted through the thickness of insulating sheet separating the optical contact from the inner surface (43d) of the insulating sheet. If the insulating sheet is not transparent enough for an efficient transmission of the light energy, then a window (43w) can be provided at the inner surface of the insulating sheet to expose the optical contact.

The LED, VCSEL or other laser diode (601a-c, 602a-c) can be fed with electrical current in the same way as described with respect to the electrode contacts (41a-c). For example, FIG. 13(b) shows an inner surface of an insulating sheet, provided with a number of diodes (601a-c, 602a-c) which are coupled to conductive tracks (44) leading to a connecting pad (20) (not shown) at the outer surface (43u) of the insulating sheet.

Various Cuff Electrode/Optrode Configurations

Figure 14:
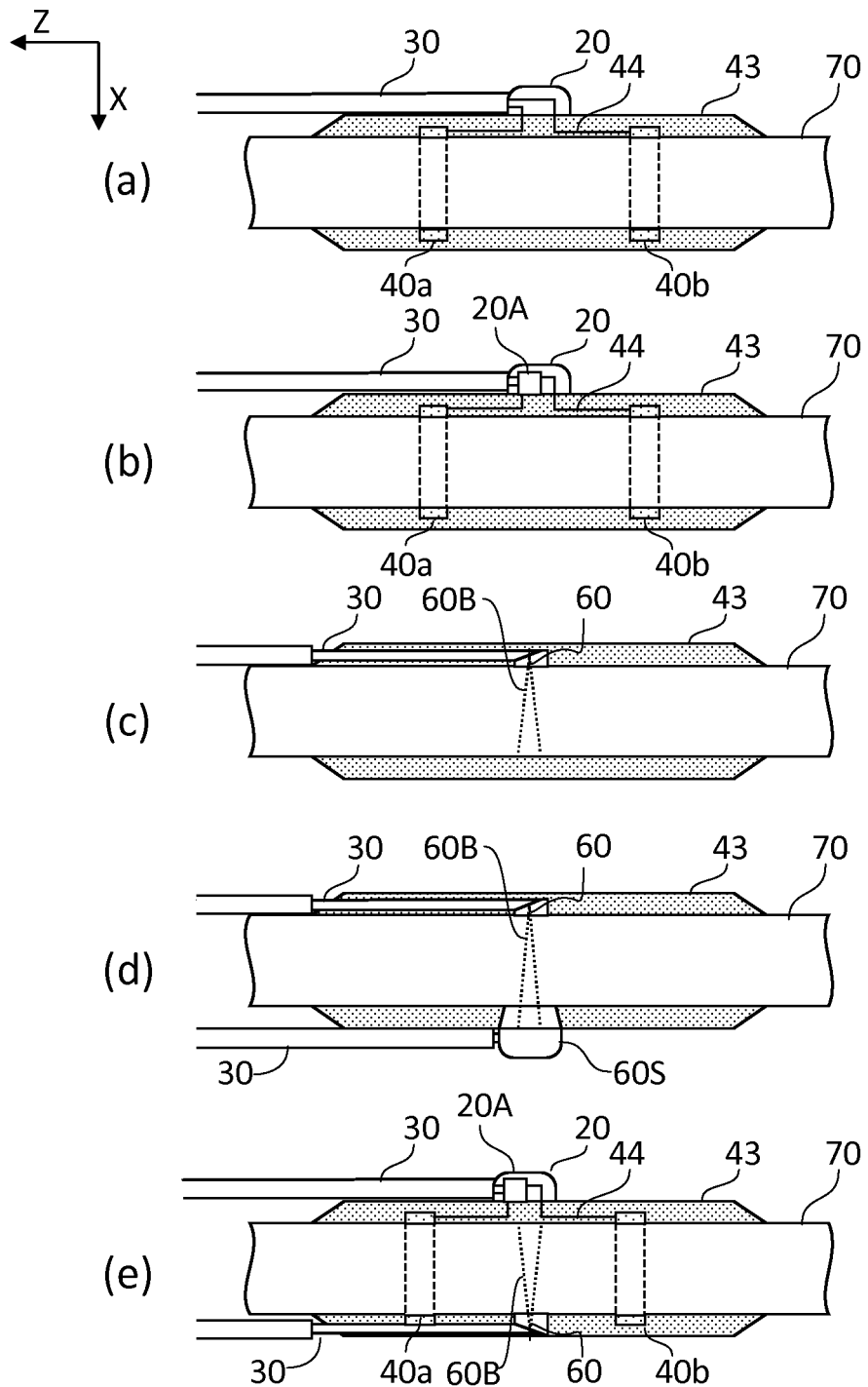
FIGS. 14(a)-14(e) show various configurations of cuff electrodes and/or cuff optrodes.

FIG. 14 illustrates various configurations of a cuff electrode/optrode according to the present invention. FIG. 14(a) illustrates a cuff electrode according to the present invention as discussed in detail supra. It comprises a lead (30) transporting energy to a connecting pad (20) whence the energy is conveyed to a first and second electrode contacts (40a, 40b). The energy can be transported from the energy pulse generator located in the housing (50) (not shown) in the form of electric energy. In this case, the connecting pad (20) is simply a contact point between the lead (30) and the conductive tracks (44). Alternatively, the energy can be transported in the form of light through a fibre optic (30) and the connecting pad comprises a photovoltaic cell able to transform the light energy into electric energy, which is fed to the first and second electrode contacts.

FIG. 14(b) shows a cuff electrode very similar to the one illustrated in FIG. 14(a), wherein the connecting pad comprises an electronic amplifier (20A) for amplifying signals of potential variations between the first and second electrodes, representative of an activity of the tissue wrapped by the cuff electrode. The cuff electrode can thus be used in a sensing mode, for detecting activity signals of a tissue. The electronic amplifier can be located in the housing (50) instead of in the connecting pad. In this embodiment, the cuff electrode of FIG. 14(a) can also be used in a sensing mode, for detecting activity signals of a tissue.

FIG. 14(c) illustrates a cuff optrode according to the present invention. In this embodiment, a fibre optic (30) coupled to a light pulse generator located in a housing (50) (not shown) is coupled to the insulating sheet (43) and is configured for driving a light beam (60B) to a precise area of the tissue to be treated. As discussed above, the end of the fibre optic can be bevelled or coupled to a lens; mirror, or other micro-optic device, adapted for guiding the light beam where desired.

FIG. 14(d) illustrates a cuff optrode very similar to the one of FIG. 14(c), further comprising a sensing optrode (60S) for sensing the light scattered, reflected or transmitted after interaction of the beam (60S) with the tissue. The optical signal thus sensed can be transmitted to the housing, either in the form of light, or of an electric signal, provided the sensing optrode is capable of transforming a light signal into an electric signal (e.g., with a photovoltaic cell).

FIG. 14(e) illustrates a cuff electrode/optrode very similar to the cuff optrode of FIG. 14(c), further comprising a first and second electrode contacts (40a, 40b) suitable for sensing activity signals of a tissue as discussed above, electrically coupled to an amplifier (20A) provided either in the housing (50) (cf. FIG. 14(a)) or in the in the connecting pad (20) (cf. FIG. 14(b)).

Process for Producing a Self-Curling Cuff Electrode

A self-curling cuff electrode according to the present invention can be produced by a process comprising the following steps:

(a) Providing an outer sheet comprising the outer surface of length, Lu, measured along the longitudinal axis, Z, and of width, Wu, measured along a transverse axis, X, normal to the longitudinal axis, Z, and further comprising an interface surface separated from the outer surface by a thickness of the outer sheet, (b) Providing an inner sheet made of a resilient material, comprising the inner surface of length, Ld, measured along the longitudinal axis, Z, and of width, Wd, measured along the transverse axis, X, and further comprising an interface surface separated from the inner surface by a thickness of the inner sheet, (c) Stretching the inner sheet along the transverse direction, X, to yield a pre-strained inner sheet, (d) Adhering the outer sheet to the pre-strained inner sheet, through their respective interface surfaces to form a support sheet having the inner surface and the outer surface, (e) Releasing the stretching of the inner sheet, and allowing the inner sheet to recover an equilibrium geometry, wherein the stretching and widths, Wu, Wd, have been selected to allow the support sheet to self-curl about the longitudinal axis, Z, resiliently forming a substantially cylindrical cuff of inner diameter, Dc, with N loops, N being comprised between 1.0 and 3.5.

The length, Ld, of the inner surface must be larger than the length, Lu, of the outer surface, and the inner surface must extend beyond the outer surface in both directions along the longitudinal axis, Z A conductive material is applied and exposed at the inner surface of the insulating support to form the at least one electrode contact (40a-c). The electrode contact can be formed by printing or otherwise depositing the conductive material onto the inner surface. Alternatively, a conductive material (e.g., in the form of a foil) can be sandwiched between the inner sheet and the outer sheet, with one or more contact windows (43w) provided in the inner sheet to expose the at least one electrode contact.

To avoid the formation of a cuff with trumpet edges, it is preferred to stretch the inner sheet also along the longitudinal direction, Z, for compensating contraction resulting from the Poisson's ratio.

In a preferred embodiment of the process of the present invention, the inner sheet has a length measured along the longitudinal axis, Z, equal to or larger than the inner length, Ld, the outer sheet has a length measured along the longitudinal axis, Z, larger than the outer length, Lu, the support sheet obtained after step (e) comprises first and second longitudinal edges extending parallel to the transverse axis, X, said first and second longitudinal edges are cut across the thickness, t, of the support sheet to form bevelled edges such that the outer surface has the outer length, Lu, and the inner surface has the inner length, Ld. The first and second longitudinal edges can be cut by machining or, preferably, by laser cutting.

Handling flaps protruding out of the inner sheet in the direction of the longitudinal axis, Z, are preferably provided. The handling flaps are preferably of a different colour from the inner sheet to facilitate visualization thereof by a surgeon.

Advantages of the Present Invention

The specific design of the edges of a cuff electrode according to the present invention has several advantages over state of the art cuff electrodes. First and foremost, the soft edges thus obtained reduce stress concentration on the tissue at the free edges of the cuff, thus preventing injuries to the cylindrical tissue.

Second, the absence of a funnel formed at the edges ensures a better tightness of the cuff electrode to body fluids ingress, and therefore allows the positioning of the electrode contacts at a shorter distance, d1, d2, from the free edges than hitherto possible. Furthermore, the distance d1, d2, must be sufficiently high to reduce leakage currents to spread out of the cuff electrode. Reducing the total cuff length makes implantation by a surgeon much easier, as the tissue must be isolated over a shorter length, reducing the risk of damaging it with the surgical tools. The substantially cylindrical tissue is also enclosed within the cuff over a shorter length.

Third, by replacing the sharp change of voltage at the cuff edges observed in state of the art cuff electrodes by a progressive change, the second derivative of the voltage profile and thus the activating function is decreased, reducing the formation of virtual electrodes stimulating the tissue outside of the boundaries of the cuff electrode. Current losses are thus decreased substantially, to the benefit of the IMD's efficacy. Current losses can be further decreased with tripolar cuff electrodes.

All the foregoing advantages are obtained without increasing the production costs of the cuff electrode.

| Ref | Feature |
|---|---|
| 20 | Connecting pad |
| 20A | Electronic amplifier |
| 30 | Lead connecting the cuff electrode to the energy pulse generator located in the housing (50) |
| 40 | Cuff electrode |
| 40a | Electrode contact |
| 40b | Electrode contact |
| 40c | Electrode contact |
| 401a-c | Discrete electrode contacts |
| 402a-c | Discrete electrode contacts |
| 43 | Electrically insulating support |
| 43d | Inner surface of the electrically insulating support |
| 43e | Edge portion of the electrically insulating support |
| 43f | Flap of the electrically insulating support |
| 43u | Outer surface of the electrically insulating support |
| 43w | Contact window in the inner surface for exposing electrode contact |
| 44 | Conductive track coupling an electrode contact to a connexion (20) |
| 44w | Connecting window in the electrically insulating support between a track (44) and a connecting pad) |
| 50 | Housing containing an energy pulse generator |
| 60 | Optical contact |
| 60B | Light beam directed by optrode |
| 60S | Sensing optrode |
| 601a-c | Discrete light emitting sources |
| 602a-c | Discrete light emitting sources |
| 70 | Cylindrical tissue, such as a nerve |
| Dc | Cuff electrode inner diameter |
| Dcm | Central lumen inner diameter |
| De | Edge lumen inner diameter |
| Dn | Substantially cylindrical tissue diameter |
| d1 | Distance of first electrode contact to first free edge |
| d2 | Distance of second electrode contact to second free edge |
| dc | Distance between first or second electrode contact with an adjacent contact |
| L | Length of the cuff electrode along Z |
| Ld | Length of the inner surface along Z |
| Lu | Length of the outer surface along Z |
| Wd | Width of the inner surface along X |
| Wu | Width of the outer surface along X |
| lc | Length of the central portion |
| le1 | Length of the first edge portion |
| le2 | Length of the second edge portion |
| tc | Mean thickness of the central portion |
| te1 | Mean thickness of the first edge portion |
| te2 | Mean thickness of the second edge portion |
| R | Radial direction |
| X | Transverse axis |
| Z | Longitudinal axis |

The invention claimed is:

1. An implantable cuff electrode and/or optrode adapted to encircle a substantially cylindrical tissue, and comprising:
a support sheet which, when deployed on a flat surface, comprises first and second longitudinal edges extending parallel to a transverse axis, X, wherein the support sheet is non-conductive and is rolled about a longitudinal axis Z, normal to the transverse axis X, thus forming a cuff of substantially cylindrical or helical geometry defining a lumen extending over a length, L, along the longitudinal axis, Z, of substantially constant inner diameter, Dc, measured along a radial axis, R, normal to the longitudinal axis, Z, wherein said cuff comprises,
an inner surface forming an interior of the cuff, and
an outer surface forming an exterior of the cuff, separated from the inner surface by a thickness of the cuff,
a central portion, extending over a length, lc, of at least 50% of the length, L, of the cuff, and having a mean central thickness, tc, measured normal to the longitudinal axis, Z, and wherein the central portion is flanked on either side by,
a first edge portion extending from a first free edge of the cuff to the central portion along the longitudinal axis, Z, and a second edge portion extending from a second free edge of the cuff to the central portion along the longitudinal axis, wherein the first edge portion has a mean edge thickness, te1, and the second edge portion has a mean edge thickness, te2,
at least a first electrode contact made of a conductive material exposed at the inner surface of the cuff, and being remote from the outer surface forming the exterior of the cuff, and/or
at least a first optical contact (60, 601a-601c) for guiding a light beam from the inner surface towards the longitudinal axis, Z,
characterized in that, the mean edge thicknesses, te1, te2, of the first and second edge portions are each lower than the mean central thickness, tc, (te1<tc and te2<tc), and in that, the inner surface of the cuff extends beyond the central outer surface in both directions along the longitudinal axis, Z, forming a slope from the first free edge of the cuff to the central portion and from the second free edge of the cuff to the central portion.

2. The implantable cuff electrode and/or optrode according to claim 1, selected among a self-curling cuff, a split cylinder cuff, and a helical cuff.

3. The implantable cuff electrode and/or optrode according to claim 1, wherein the support sheet is formed of an outer sheet comprising the outer surface, adhered to an inner sheet comprising the inner surface wherein said inner sheet has the inner length, Ld>Lu, and said outer sheet has the outer length, Lu, and wherein the inner sheet extends beyond the outer sheet in both directions along the longitudinal axis, Z, and the inner sheet defines the first and second longitudinal edges of the support sheet.

4. The implantable cuff electrode and/or optrode according to claim 2, wherein the first and second longitudinal edges of the support sheet are bevelled across the thickness, such that the outer surface has an outer length, Lu, and the inner surface has an inner length, Ld>Lu.

5. The implantable cuff electrode and/or optrode according to claim 2, forming a self-curling cuff, wherein the support sheet is formed of an outer sheet comprising the outer surface, adhered to an inner sheet comprising the inner surface, and wherein said inner sheet is made of a resilient material and is resiliently pre-strained along a transverse axis, X, normal to the longitudinal axis, Z, to create a bias suitable for self-curling the support sheet about the longitudinal axis, Z, to resiliently form a substantially cylindrical self-curling cuff comprising the lumen of substantially constant inner diameter, Dc.

6. The implantable cuff electrode and/or optrode according to claim 1, wherein
the length, lc, of the central portion is at least 65% of the length, L, of the cuff, and is less than 95% of the length, L, of the cuff, and/or
the first and second edge portions have a length, lei, Ie2, respectively, measured along the longitudinal axis, Z, wherein each of lei and Ie2 is at least equal to 0.5 mm, and wherein each of lei and Ie2 is not more than 5.0 mm.

7. The implantable cuff electrode and/or optrode according to claim 1, wherein when deployed on a flat surface,
(a) the outer surface has an outer width, Wu, measured along the transverse axis, X, normal to the longitudinal axis, Z,
(b) the inner surface has an inner width, Wd, measured along a transverse axis, X, normal to the longitudinal axis, Z,
wherein the inner width, Wd, is substantially equal to the outer width, Wu (Wd≅Wu).

8. The implantable cuff electrode and/or optrode according to claim 1, wherein
the implantable cuff electrode and/or optrode forms a self-curling cuff and wherein the support sheet has a bias and inner and outer width, Wd, Wu, such that the support sheet self-curls into the substantially 5 cylindrical cuff of inner diameter, Dc, with N loops, with N being comprised between 1 and 3.5, or
the implantable cuff electrode and/or optrode forms a split cylinder cuff, wherein the inner and outer widths, Wd, Wu, of the support sheet are such that the support sheet forms the substantially cylindrical cuff of inner diameter, Dc, with N loops, with N being comprised between 0.7 and 1.2, or
the implantable cuff electrode and/or optrode forms a helical cuff, comprising n=1 to 3 support sheets, wherein each of the n support sheets has an inner and outer widths, Wd, Wu, such that each support sheet forms a helix of N coils, with N being comprised between 1 and 5.

9. The implantable cuff electrode and/or optrode according to claim 1, comprising a first and a second electrode contacts to form a bipolar electrode, and preferably a third electrode contact to form a tripolar electrode.

10. The implantable cuff electrode and/or optrode according to claim 1, comprising a first electrode contact, and wherein the first electrode contact is in the form of,
a continuous strip extending transverse to the longitudinal axis, Z, when the support sheet is deployed on a flat surface, at least along the portion of the inner surface forming the interior of the cuff, or
discrete electrode contact elements distributed transverse to the longitudinal axis, Z, when the support sheet is deployed on a flat surface, at least along the portion of the inner surface forming the interior of the cuff.

11. The implantable cuff electrode and/or optrode according to claim 1, comprising a first optical contact selected among a fibre optics, preferably comprising a cleaved and polished end or coupled to a lens or mirror, or a light source including a LED, VCSEL, laser diode, the implantable cuff electrode and/or optrode preferably further comprising a light sensing unit for sensing light transmitted, reflected, scattered, or a combination thereof from the light beam.

12. The implantable cuff electrode and/or optrode according to the preceding claim 11, comprising at least one electrode contact.

13. A process for producing an implantable self-curling cuff electrode and/or optrode according to claim 2, comprising,
(a) providing an outer sheet comprising the outer surface of length, Lu, measured along the longitudinal axis, Z, and of width, Wu, measured along the transverse axis, X, normal to the longitudinal axis, Z, and further comprising an interface surface separated from the outer surface by a thickness of the outer sheet,
(b) providing an inner sheet made of a resilient material, comprising the inner surface of length, Ld, measured along the longitudinal axis, Z, and of width, Ws, measured along the transverse axis, X, and further comprising an interface surface separated from the inner surface by a thickness of the inner sheet, the inner sheet further comprising at least one contact window bringing the inner surface in fluid communication with the interface surface, (c) applying a conductive material or an optical contact between the outer sheet and the inner sheet, (d) stretching the inner sheet along the transverse direction, X, to yield a pre strained inner sheet, and optionally stretching the inner sheet also along the longitudinal direction, Z, to yield an inner sheet pre-strained biaxially, (e) adhering the outer sheet to the pre-strained inner sheet, through their respective interface surfaces to form the support sheet having first and second longitudinal edges extending parallel to the transverse axis, X, and having the conductive material or an optrode sandwiched between the outer sheet and the inner sheet, in registry with the at least one contact window, (f) releasing the stretching of the inner sheet, and allowing the inner sheet to recover an equilibrium geometry, wherein the stretching and widths, Wu, Wd, have been selected to allow the support sheet to self-curl about the longitudinal axis, Z, resiliently forming a substantially cylindrical cuff defining a lumen extending over the length, L, along the longitudinal axis, Z, of substantially constant inner diameter, Dc, measured along the radial axis, R, normal to the longitudinal axis, Z, with N loops, N being comprised between 1.0 and 3.5, characterized in that, the length, Ld, of the inner surface is larger than the length, Lu, of the outer surface, and in that, the inner surface extends beyond the outer surface in both directions along the longitudinal axis, Z.

14. The process according to claim 13, wherein the inner sheet has the inner length, Ld, and the outer sheet has the outer length, Lu, and wherein the inner sheet is adhered to the outer sheet such that the inner sheet extends beyond the outer sheet in both directions along the longitudinal axis, Z, and the inner sheet defines the first and second longitudinal edges of the support sheet.

15. A process according to claim 13, wherein
the inner sheet has a length measured along the longitudinal axis, Z, equal to or larger than the inner length, Ld,
the outer sheet has a length measured along the longitudinal axis, Z, larger than the outer length, Lu,
the first and second longitudinal edges are cut across the thickness, t, of the support sheet to form bevelled edges such that the outer surface has the outer length, Lu, and the inner surface has the inner length, Ld, the first and second longitudinal edges can be cut by machining or by laser cutting.

* * * * *